(12) United States Patent
Masotti et al.

(10) Patent No.: US 11,147,625 B2
(45) Date of Patent: Oct. 19, 2021

(54) DEVICE FOR LASER THERMAL ABLATION WITH CENTERING MEANS AND EQUIPMENT COMPRISING SAID DEVICE

(71) Applicant: ELESTA S.R.L., Calenzano (IT)

(72) Inventors: Leonardo Masotti, Sesto Fiorentino (IT); Luca Breschi, Vaiano (IT)

(73) Assignee: ELESTA S.R.L., Calenzano (IT)

( * ) Notice: Subject to any disclaimer, the term of this patent is extended or adjusted under 35 U.S.C. 154(b) by 63 days.

(21) Appl. No.: 16/348,639

(22) PCT Filed: Nov. 3, 2017

(86) PCT No.: PCT/EP2017/078232
§ 371 (c)(1),
(2) Date: May 9, 2019

(87) PCT Pub. No.: WO2018/087013
PCT Pub. Date: May 17, 2018

(65) Prior Publication Data
US 2019/0321100 A1    Oct. 24, 2019

(30) Foreign Application Priority Data

Nov. 10, 2016    (IT) .................. 102016000113574

(51) Int. Cl.
*A61B 18/24*        (2006.01)
*A61B 18/00*        (2006.01)
*A61B 18/20*        (2006.01)
*A61B 18/22*        (2006.01)

(52) U.S. Cl.
CPC ............. *A61B 18/24* (2013.01); *A61B 2018/00023* (2013.01); *A61B 2018/00577* (2013.01); *A61B 2018/2005* (2013.01); *A61B 2018/2261* (2013.01)

(58) Field of Classification Search
CPC .......... A61B 18/20; A61B 2018/00023; A61B 2018/00029; A61B 2018/00035; A61B 2018/00065; A61B 2018/0013; A61B 2018/00577; A61B 2018/2261; A61B 2018/2272; A61B 90/39; A61B 18/22; A61N 5/0601
See application file for complete search history.

(56) References Cited

U.S. PATENT DOCUMENTS

| 5,409,483 A | 4/1995 | Campbell et al. |
| 7,270,656 B2 | 9/2007 | Gowda et al. |
| 2006/0217693 A1 | 9/2006 | Gowda et al. |

(Continued)

FOREIGN PATENT DOCUMENTS

EP    3 058 888 A1    8/2016

*Primary Examiner* — Jon Eric C Morales
(74) *Attorney, Agent, or Firm* — McGlew and Tuttle, P.C.

(57) ABSTRACT

The device comprises: —an outer tubular structure (21) having a closed terminal end; —an inner tubular structure (23), positioned in the outer tubular structure, having a terminal end and defining an inner volume, configured to receive a light guide. A first coolant circulation gap (25) is formed between the outer tubular structure and the inner tubular structure. Between the outer tubular structure (21) and the inner tubular structure (23) a first spacer (33) is located, which develops helically around the longitudinal axis (A-A) of the outer tubular structure (21).

22 Claims, 18 Drawing Sheets

(56) References Cited

U.S. PATENT DOCUMENTS

| | | |
|---|---|---|
| 2008/0043790 A1 | 2/2008 | Gruzdev et al. |
| 2009/0048588 A1 | 2/2009 | Peng et al. |
| 2010/0262137 A1 | 10/2010 | Nye et al. |
| 2011/0230872 A1 | 9/2011 | Griffin et al. |
| 2012/0259326 A1 | 10/2012 | Brannan et al. |
| 2016/0279388 A1* | 9/2016 | Barrish ............. A61M 25/1034 |

* cited by examiner

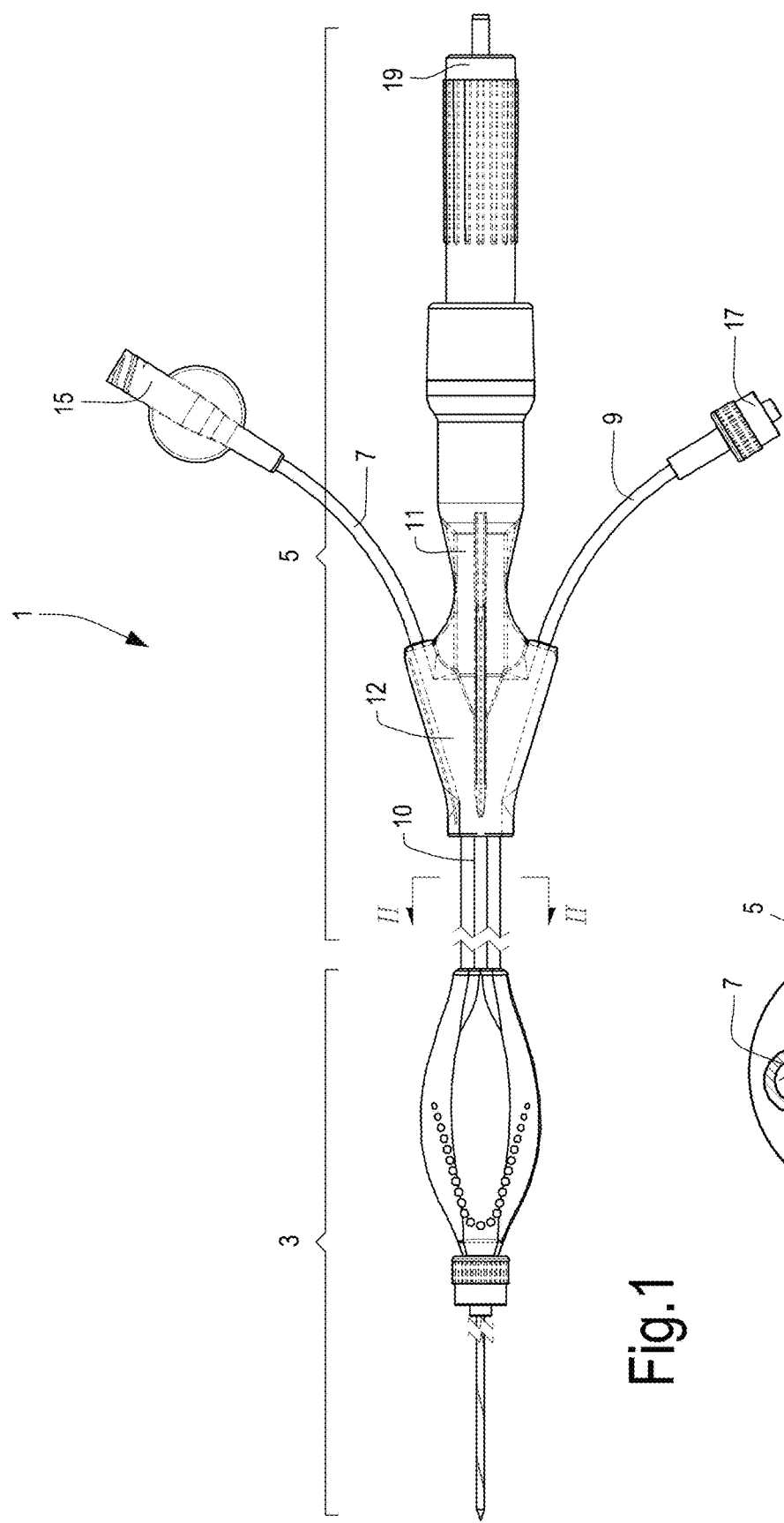
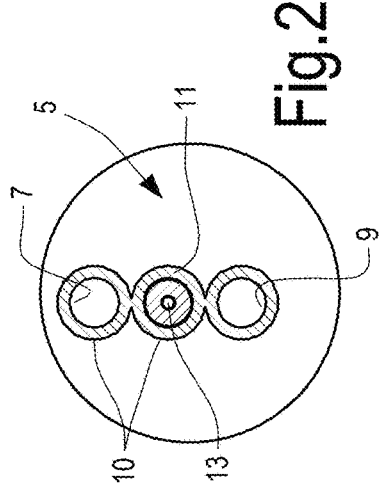
Fig.1
Fig.2

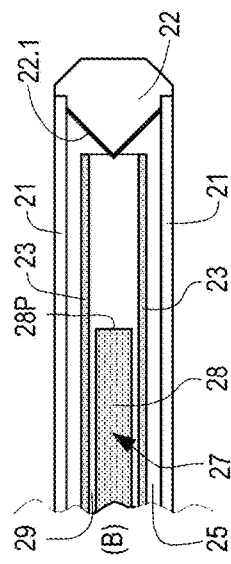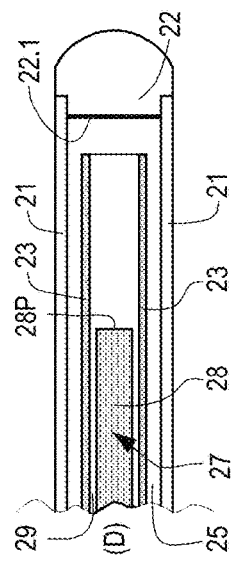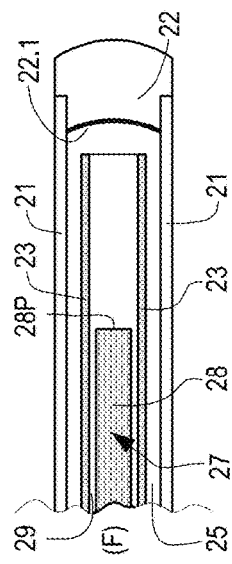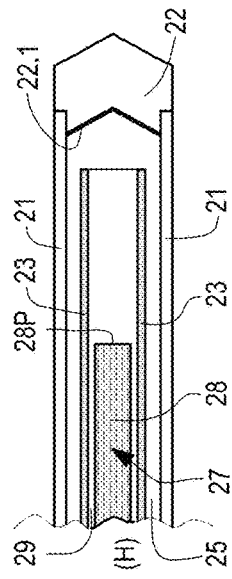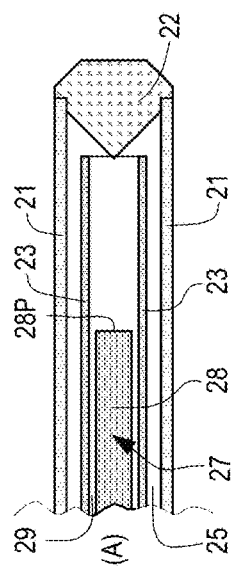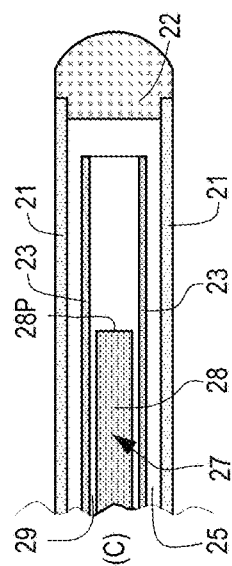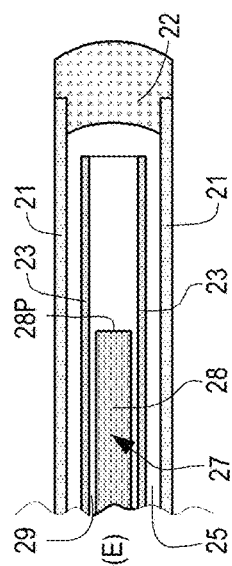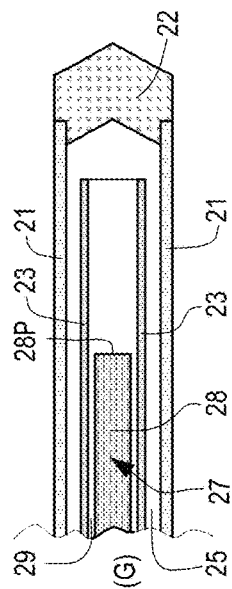
Fig.12

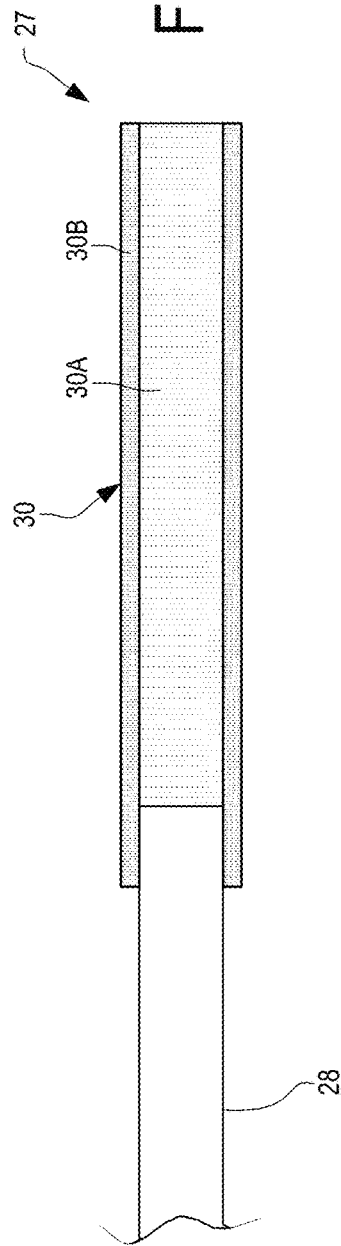
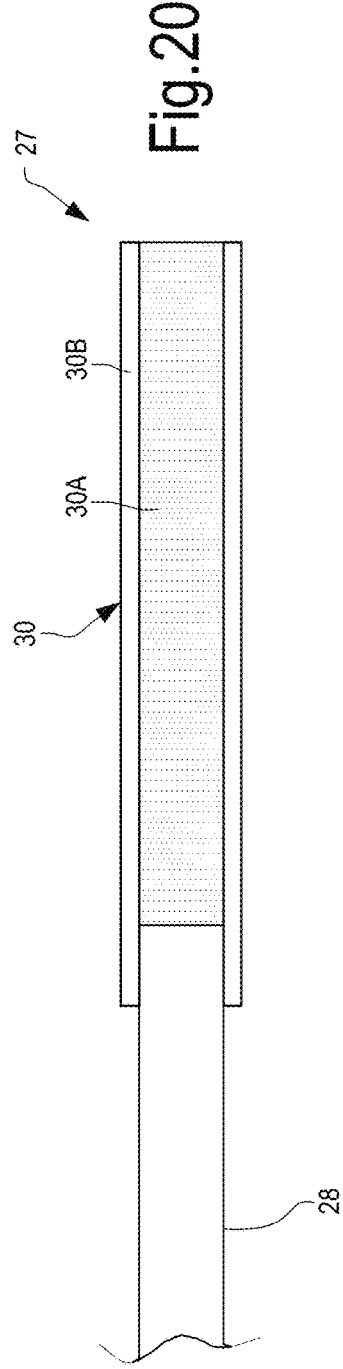
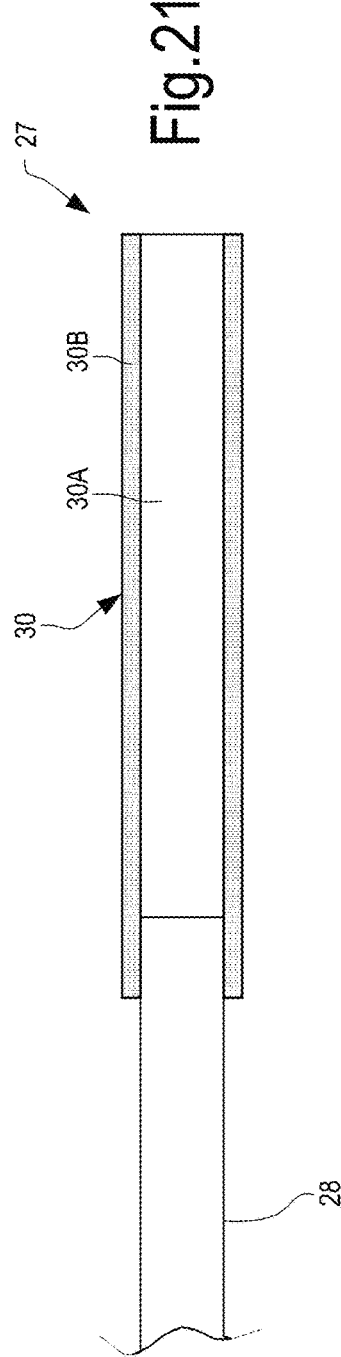

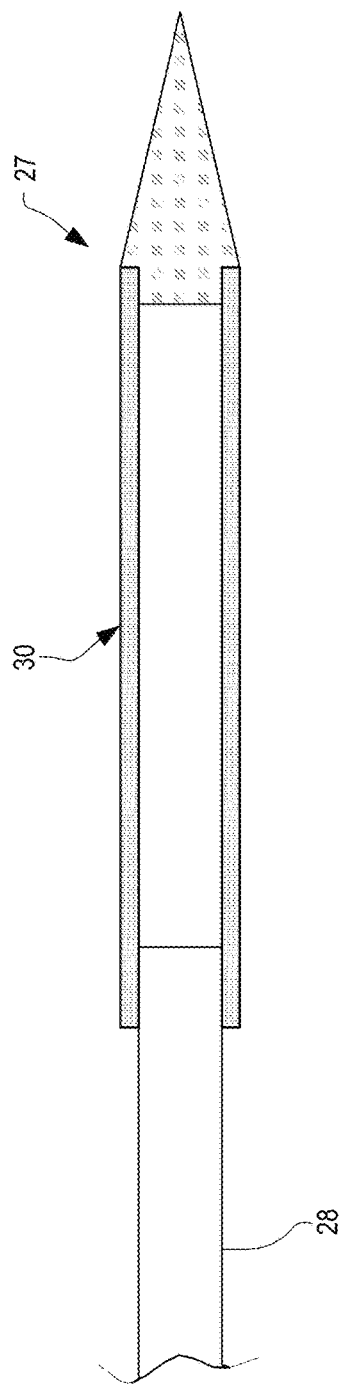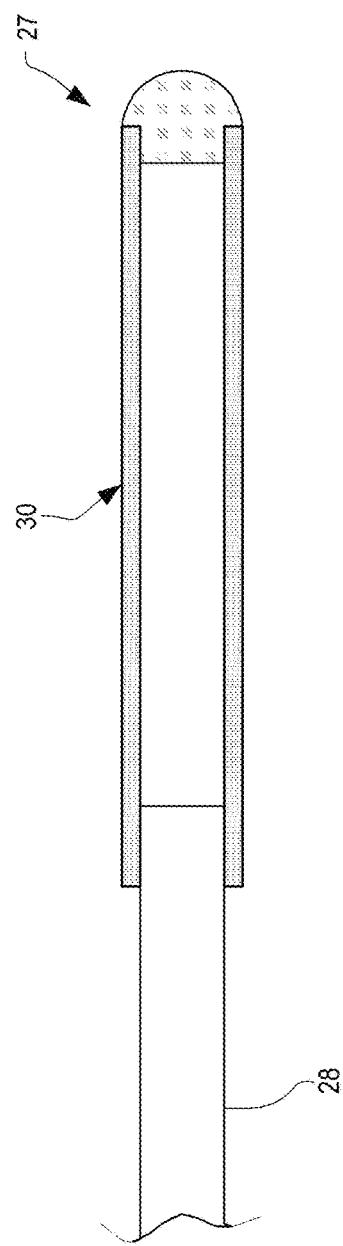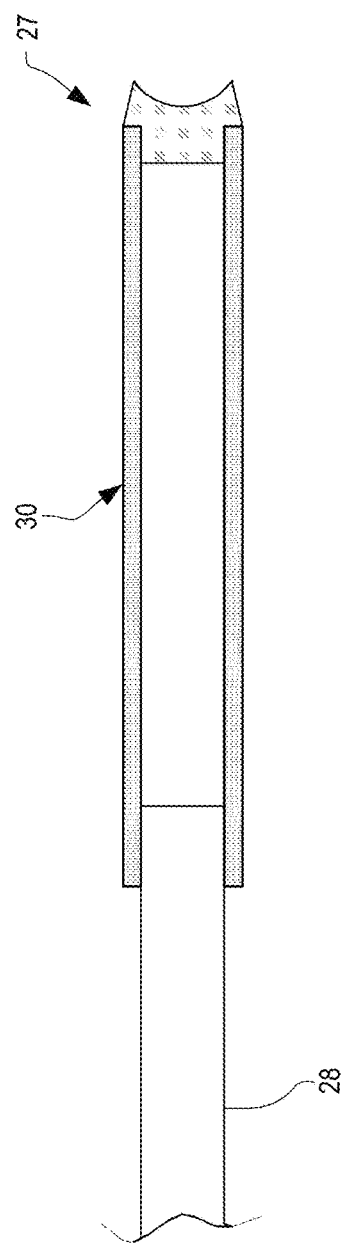

DEVICE FOR LASER THERMAL ABLATION WITH CENTERING MEANS AND EQUIPMENT COMPRISING SAID DEVICE

TECHNICAL FIELD

This invention relates to medical devices and equipment for thermal ablation treatments. Embodiments described here relate to laser thermal ablation systems.

BACKGROUND ART

Thermal ablation is frequently used in medicine to remove tissue, for example solid cancer tissue, via a mini-invasive approach. Several forms of energy have already been used in this field, including radio frequency, microwaves and lasers. Other methods use cryoablation, i.e. destruction of parts of pathological tissue using cooling cycles, or irreversible electroporation, which applies electrical pulses to damage the cell membrane in an irreversible manner.

In the field of laser thermal ablation, devices are used, which comprise a catheter that forms an insertion needle through which a fiber is inserted into the area to be treated.

In substance, to destroy the cancer cells, an electromagnetic radiation, typically a laser radiation, is carried into the cancerous mass. To reach the cancerous mass, a device is provided that has a catheter or a pervious needle within which an optical fiber is guided. In certain cases, the optical fiber is positioned in the point in which the laser radiation must be applied and the catheter is retracted. The naked fiber is in direct contact with the tissues, which are irradiated with the electromagnetic radiation. In other known embodiments, the fiber is guided in a catheter and remains inside it, said catheter being made of material that allows the passage of the laser radiation. A coolant circulates in the catheter to remove heat and avoid tissue carbonization phenomena.

To treat larger volumes of tissue, a plurality of optical fibers is used, each one guided into position using an insertion needle. Currently, the standard of ablation with a flat tip fiber envisages the use of 5 W and a dose of 1200-1800J. To increase the volume in a transversal direction with respect to the axis of the fiber, the insertion of several optical fibers is resorted to, while if the ablation volume is to be increased in an axial direction this involves a maneuver retracting the fiber and releasing a plurality of doses of energy in sequence.

One of the main limits to obtaining large volumes of ablation with a naked fiber applicator is the formation of a carbonization layer that is created in the wall of the cavity left by sublimation of the tissue in the area proximal to the fiber, and a severe dehydration in the first portion of tissue behind the carbonization. These phenomena hinder diffusion of the laser light to the distal portions of the tumor, limiting the effectiveness of the device. Hindrance to diffusion of the light and heat developed in the tissues closest to the fiber means that the temperatures raise in these portions close to the tip of the fiber, with consequent sublimation of the tissues. This change in phase consumes laser energy that might otherwise contribute to denaturing the tissues in the distal areas. Consequently, for an equivalent total amount of energy delivered, the volume undergoing the desired treatment is less. Further administration of energy basically contributes to increase the sublimation of tissues closest to the tip of the fiber, which rise to higher temperatures, without contributing towards increasing the volume treated.

Carbonization takes place due to a high density of power on the tip of the fiber and in the space closest to it, where dehydration takes place and drying and sublimation of the tissue occur, producing a carbonized cavity and a ring of coagulated surrounding tissue. This creates a barrier to thermal diffusion towards the tissues further away from the tip of the fiber. It is not possible to increase the power delivered in order to deliver thermal energy beyond the carbonized and coagulated area, as using frontal emission of the optical fiber produces long, narrow lesions that are incompatible with the rounded form generally seen in tumor masses. Furthermore, an increase in the power of the laser beyond optimal values results in a worsening of the process of irreversible damage to cells that the thermal ablation is trying to achieve. In effect, at higher powers a rapid increase in temperature is provoked in the areas closest to the fiber, which dehydrate rapidly, drying out because they are not supplied with fluids by the areas further away. The severely dehydrated areas of tissue become opaque to the transmission of laser light and hinder propagation of the heat in the surrounding volume.

To solve these problems, cooled thermal ablation devices have been created, in which a coolant circulates in the catheter in which the fiber is inserted and removes heat. More specifically, cooled devices of a known type comprise an external catheter having a closed distal end, inside which a duct is arranged that houses a light guide, typically an optical fiber. Between the inner duct and the outer catheter a gap is defined, in fluid communication with a second gap defined between the inner duct and the optical fiber. The coolant circulates in the two gaps. The coolant removes heat from the treatment area, avoiding overheating and carbonization of the tissue surrounding the fiber.

U.S. Pat. No. 7,270,656 describes a device for laser thermal ablation comprising: an outer tubular structure having a closed terminal end and an inner longitudinal cavity; and an inner tubular structure having a side wall that defines an inner longitudinal volume terminating with a terminal end. A light guide is inserted inside the inner tubular structure, to carry a laser radiation to the terminal end. The inner tubular structure extends longitudinally in the inner longitudinal cavity of the outer tubular structure. A first coolant circulation gap is formed between the outer tubular structure and the inner tubular structure. The terminal end of the inner tubular structure is open to put into fluid communication the gap and the inner volume of the inner tubular structure, to remove heat from the treatment area. In this way, an improvement in the effectiveness of the device is achieved.

The inner tubular structure and the outer tubular structure must be kept substantially coaxial to each other. To that end, some spacers, extruded together with one or the other of the two tubular structures, are arranged in the gap formed between the inner tubular structure and the outer tubular structure. These spacers reduce the working section for passage for the coolant, making the device less efficient.

Consequently, there is a need to create more efficient thermal ablation devices that solve either fully or in part at least one of the limits and problems in known devices.

SUMMARY OF THE INVENTION

According to a first aspect, a device for laser thermal ablation is provided, comprising: an outer tubular structure having a closed terminal end; an inner tubular structure, positioned in the outer tubular structure, having a terminal end and defining an inner volume, configured to receive a light guide. A first gap is formed between the outer tubular structure and the inner tubular structure, for circulation of a coolant, in fluid communication with the inner volume of the inner tubular structure. To achieve better operation of the device, in particular to obtain more uniform lateral irradiation of an electromagnetic radiation, typically laser radiation, coming from the inside of the inner tubular structure, a first spacer, developing helically around the longitudinal axis of the outer tubular structure, is positioned between the outer tubular structure and the inner tubular structure. The helical development of the spacer reduces the negative effect of the spacer on the flow of coolant.

According to other embodiments, a device for laser thermal ablation is provided, comprising: an outer tubular structure having a closed terminal end; an inner tubular structure, positioned in the outer tubular structure, having a terminal end and defining an inner volume; a light guide housed in the volume of the inner tubular structure; wherein between the outer tubular structure and the inner tubular structure a first coolant circulation gap is formed; and wherein between the inner tubular structure and the light guide a second coolant circulation gap is formed. To maintain the inner tubular structure and the light guide located inside the latter substantially coaxial to each other, a second spacer is placed in the gap formed between the inner tubular structure and the light guide, helically developing around the longitudinal axis of the inner tubular structure.

In particularly advantageous embodiments, both the first helical spacer and the second helical spacer are provided. In particular, the two helical spacers may have windings in opposite directions.

Known devices typically envisage at least three straight spacers parallel to the axis of the outer tubular structure, having the purpose of maintaining the outer tubular structure and the inner tubular structure coaxial to each other. The presence of this high number of spacers significantly reduces the section for passage of the coolant. In a similar way, at least three straight spacers are envisaged between the light guide and the inner tubular structure, to maintain the light guide coaxial with the inner tubular structure.

Unlike the known solutions, according to the embodiments described here a spacer is used, preferably in the form of a single thread, which wraps helically around the axis of the inner and outer tubular structures. In this way the section for passage of the coolant fluid is reduced to a lesser extent by the presence of the spacer, which still has a form that will guarantee the coaxial position of the inner tubular structure and the outer tubular structure. The helical shape of the spacer is such that the coaxial positioning is obtained using a single spacer element, rather than a plurality (at least three) of spacers parallel to the axis of the inner and outer tubular structures, as is the case in the devices according to the current art.

In a similar way, a helical spacer can be positioned between the light guide and the inner tubular structure.

Using a first helical spacer in the gap between the two tubular structures and a second helical spacer in the gap between the inner tubular structure and the light guide maximizes the advantages in terms of impact on the condition of the coolant flow.

While in known systems the spacers are typically formed by extrusion together with one or the other of the concentric tubular structures, as described here the straight element with helical development may be applied to the outer surface of the inner tubular structure after this has been formed, for example by extrusion. This allows the spacer to be arranged only in the area, in which its presence is necessary or useful, that is to say typically in the distal area of the device, where there is irradiation and diffusion of the electromagnetic radiation from the inside of the device to the outside, into the tissue, in which the device has been inserted.

The outer tubular structure and the inner tubular structure have at least one portion diffusing and/or transparent to the electromagnetic radiation carried by the light guide housed in the inner tubular structure.

The second spacer and the first spacer may be present in a limited portion of the device, preferably in the area in which the electromagnetic radiation carried by the guide is diffused to the outside of the device. In effect, the at least approximate concentricity or coaxiality between the tubular structures and the light guide is particularly important in the area in which irradiation of the surrounding tissues occurs.

By creating one, the other or both the first spacer and the second spacer separately and not by extrusion together with the tubular structures, it is possible to restrict the extension of the spacer to the area where it is actually important to guarantee concentricity or coaxiality. In this way the negative incidence of the spacer on the flow conditions of the coolant is further reduced.

Preferably, to achieve more effective circulation of the coolant, the side wall of the inner tubular structure comprises more than one aperture or opening for passage of the coolant. In advantageous embodiments, a plurality of lateral openings are provided, putting the first gap into fluid connection with the inner volume of the inner tubular structure. Conveniently, the lateral openings may be positioned, with respect to the helical spacers, in such a way that the latter do not obstruct passage of the coolant through the lateral apertures or openings.

To obtain a uniform flow the openings or apertures formed in the wall of the inner tubular structure are preferably arranged in a staggered position around a longitudinal axis of the inner tubular structure.

In advantageous embodiments the lateral openings are arranged in sequence along the longitudinal extension of the inner tubular structure.

The terminal end of the inner tubular structure may be open so that the flow of coolant can pass both through the lateral openings formed in the wall of the inner tubular structure, and through the open end of the latter. However, in preferred embodiments, better circulation of the coolant is obtained if the terminal end of the inner tubular structure is closed. In this way the coolant only flows through the lateral openings.

In some embodiments, the light guide may comprise an optical fiber, which may extend up to the terminal end of the inner tubular structure or may have a distal end positioned inside the inner tubular structure at a certain distance from the terminal end of the inner tubular structure. The tip of the optical fiber and/or a portion of its lateral surface adjacent to the distal end may be machined to obtain diffusion of the electromagnetic radiation, typically a laser radiation, carried along the optical fiber.

In other embodiments it can be envisaged that the optical fiber be combined with a diffuser positioned between the terminal end of the fiber and the terminal end of the inner tubular structure. The diffuser has a shape and/or a surface machining and/or is made of a material containing diffusing particles, to promote diffusion of the electromagnetic radiation from the inside of the diffuser to the outside of the diffuser.

In certain embodiments, the diffuser comprises a central core and an outer sheath surrounding the core. The sheath, or the core, or both may be diffusing to a wavelength of an electromagnetic radiation propagating in the light guide.

In advantageous embodiments, the core is made using a material that is transparent at the wavelength of electromagnetic radiation propagated in the light guide, while the sheath is made using a diffusing material. In this way manufacture of the diffuser is simplified. To increase the quality of the diffusion of electromagnetic radiation, obtaining more uniform radiation, according to advantageous embodiments the diffuser has a curved shape, in particular an approximately helical shape, in at least one portion of its longitudinal development. For example, the diffuser may have a straight section and a helical section, forming one or more windings around a geometric axis substantially corresponding to the longitudinal axis of the inner tubular structure.

When the device has an optical fiber configured to diffuse the electromagnetic radiation laterally and/or comprises a diffuser configured to diffuse the electromagnetic radiation laterally, the inner tubular structure and the outer tubular structure can be made in a material that is simply transparent to the electromagnetic radiation carried along the light guide that is housed in the inner tubular structure.

In some embodiments, however, it can be envisaged for one, the other or both said outer tubular structure and inner tubular structure be made in such a way as to diffuse the electromagnetic radiation propagated in the light guide.

For example, it is possible to provide a light guide comprising an optical fiber that terminates at a certain distance from the terminal end of the inner tubular structure, and that emits a beam of electromagnetic radiation, typically a beam of laser radiation, from its tip. The tip may be machined to obtain a beam with a sufficient angular aperture. The diverging beam is incident on the inner surface of the inner tubular structure which, if made of diffusing material, promotes uniform diffusion of the electromagnetic radiation towards the outer tubular structure. The latter may be transparent or likewise diffusing to the electromagnetic radiation. In other embodiments, the inner tubular structure may be transparent to the electromagnetic radiation used, while the outer tubular structure is diffusing.

The inner tubular structure and/or the outer tubular structure may be rendered diffusing by means of a suitable mechanical surface machining or chemical surface treatment. In certain embodiments the outer tubular structure and/or the inner tubular structure may be rendered diffusing by the addition of suitable diffusing particles or powder in the base material from which the inner and/or outer tubular structure is formed. The base material may be quartz, glass, resin or another polymer material. The diffusing material may be a micrometric or sub micrometric powder, for example hydroxylapatite, TiO, $TiO_2$, $Al_2O_3$. To these can be added, for example, Barium sulphate ($BaSO_4$) which also has radio-opacity properties that allow viewing of the device using X ray imaging techniques.

In some embodiments, the terminal end of the outer tubular structure is closed by a closing element made of a material that diffuses at the wavelength of the electromagnetic radiation propagating in the light guide. In this way propagation of the electromagnetic radiation is also achieved frontally. In other embodiments, the closing element may be opaque to the electromagnetic radiation used, in which case the electromagnetic radiation only diffuses into the surrounding tissues radially with respect to the axis of the outer tubular structure. In yet other embodiments the closing element on the terminal end of the outer tubular structure may have a reflecting surface facing towards the inside of the tubular structure itself. In this way the electromagnetic radiation incident on the closing element is reflected back and may diffuse into the tissues through the lateral wall of the outer tubular structure.

As previously noted, the temperature reached in the treatment area may represent a critical parameter, as in order to obtain denaturation of the tumor cells it is necessary to reach a sufficiently high temperature. However, high temperatures bring about carbonization of the tissues and therefore hinders propagation of the electromagnetic radiation. To achieve better control during the treatment phase, some embodiments of the device envisage a temperature sensor associated with the outer tubular structure. The temperature sensor may be a thermocouple, a thermistor, or any other suitable sensor. The temperature sensor is preferably housed inside the outer tubular structure, to be mechanically protected.

According to a further aspect, an apparatus for laser thermal ablation is described here, comprising: a device as described above; a laser source; a cooling circuit; a control unit.

The apparatus may also comprise one or more of the following elements, components or devices: a pump for circulation of the coolant; a flow meter, configured to detect the flow rate of coolant; a pressure sensor configured to detect the pressure of the coolant in at least one point of the cooling circuit; a tank for feeding the coolant to the device; a tank for collecting the coolant from the device; a tank for storing and recirculating the coolant; a member for removing heat from the coolant.

BRIEF DESCRIPTION OF THE DRAWINGS

The invention will be better understood following the description and the enclosed drawings, which show non-limiting practical embodiments of the invention. More specifically, the drawing show:

FIG. 1 an overall view of a device according to one embodiment;

FIG. 2 a cross-section along line II-II of FIG. 1;

FIGS. 12A-12H embodiments of a terminal element closing the catheter;

FIGS. 19, 20, 21 alternative embodiments of the light guide and in particular of the terminal diffuser thereof;

FIGS. 23A-23C embodiments of the terminal element of the light guide.

DETAILED DESCRIPTION OF EMBODIMENTS

Figure 3:
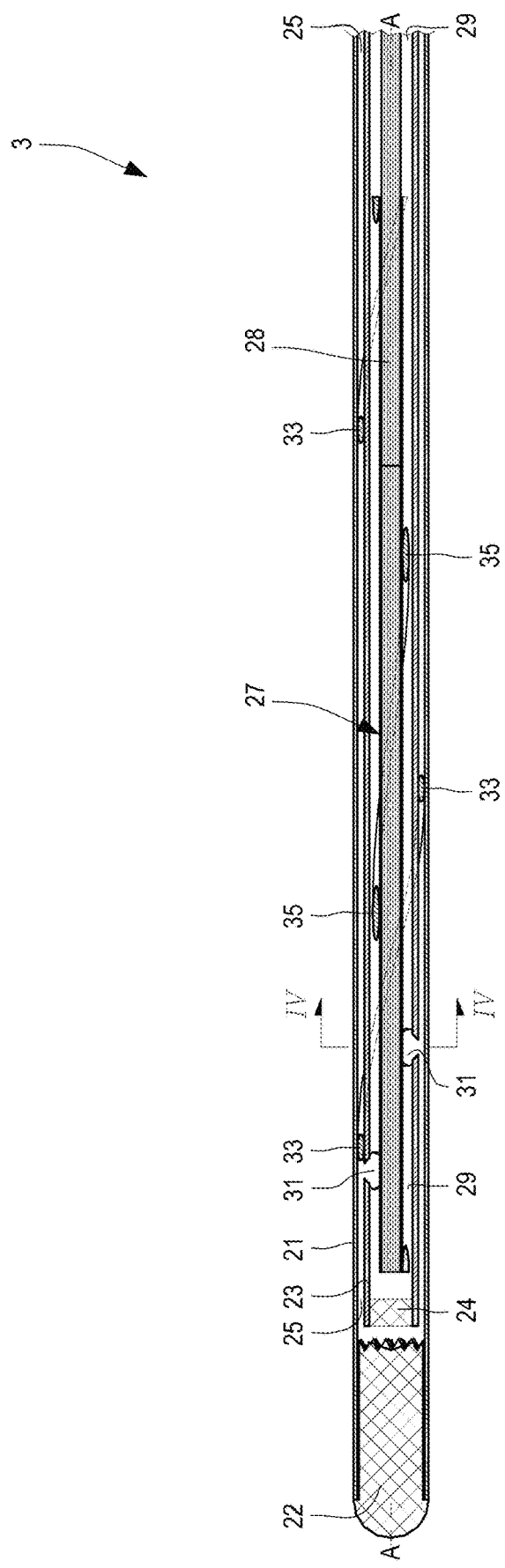
FIG. 3 a cross-section according to a plane containing the longitudinal axis of the catheter forming the distal element of the device shown in FIG. 1.

The following detailed description of the exemplary embodiments refers to the accompanying drawings. The same reference numbers in different drawings identify the same or similar elements. Additionally, the drawings are not necessarily drawn to scale. Also, the following detailed description does not limit the invention. Instead, the scope of the invention is defined by the appended claims.

Reference throughout the specification to "one embodiment" or "an embodiment" or "some embodiments" means that the particular feature, structure or characteristic described in connection with an embodiment is included in at least one embodiment of the subject matter disclosed. Thus, the appearance of the phrase "in one embodiment" or "in an embodiment" or "in some embodiments" in various places throughout the specification is not necessarily referring to the same embodiment(s). Further, the particular features, structures or characteristics may be combined in any suitable manner in one or more embodiments. With initial reference to FIG. 1, reference number 1 indicates a device according to the invention, in a first embodiment. The device 1 comprises a distal part 3 and an optical-hydraulic connection 5 to an apparatus, described below, containing a laser source. The optical-hydraulic connection 5 may comprise three channels, illustrated in more detail in the cross-section of FIG. 2. A first channel 7 and a second channel 9 serve to allow circulation of a coolant inside a catheter, described below, forming part of the distal portion 3 of the device 1. A third channel 11 serves to allow passage of a light guide, for example an optical fiber 13. In some embodiments, as described below in greater detail, a connection to a temperature sensor, which is found in the distal end of the catheter of device 1, may also pass through channel 11.

In the embodiment illustrated in FIGS. 1 and 2 the channels 7, 9 and 11 are substantially on the same plane, and the channel 11 is arranged between channels 7 and 9. In this way, channels 7 and 9 are spaced from each other, to limit mutual heat exchange. Channels 7, 9 and 11 are closed within a flexible tube 10, forming a common sheath that holds all the channels 7, 9 and 11 together up to a terminal element 12 from which channels 7, 9 and 11 depart separately, terminating with respective connectors 15, 17 and 19. These connectors serve to connect the device 1 to the apparatus containing a laser source, to inject a laser radiation into the optical fiber 13, and a cooling circuit that causes a coolant to circulate through channels 7 and 9.

Figure 4:
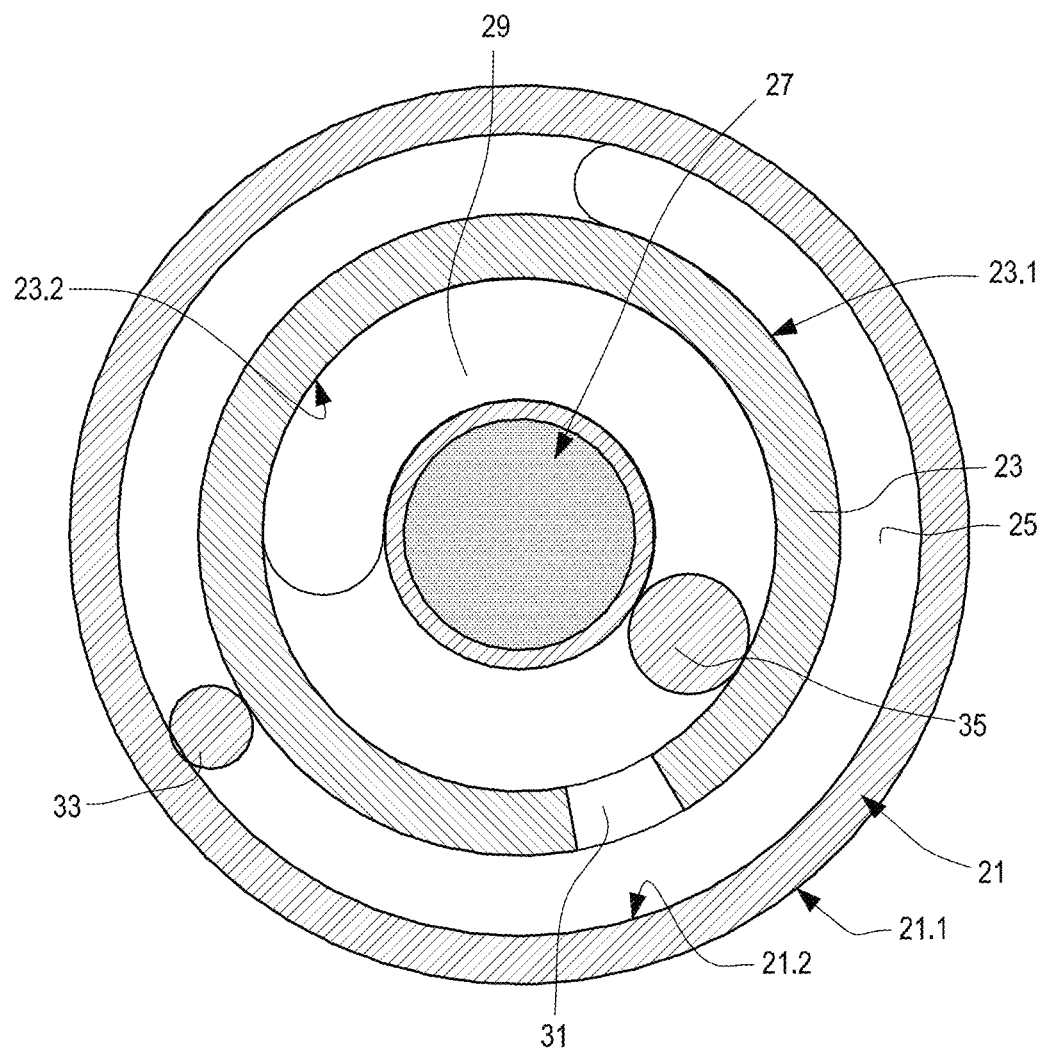
FIG. 4 a transversal cross-section along line IV-IV of FIG. 1.

FIG. 3 illustrates the distal portion 2 of the device 1 in a cross-section according to a plane containing the longitudinal axis, and FIG. 4 shows a transversal cross-section of said distal portion along line IV-IV of FIG. 3.

The distal portion of device 1 comprises an outer tubular structure 21, consisting for example of a catheter or a needle. The terminal end of the outer tubular structure 21 is closed by a closing element 22. In the following the outer tubular structure 21 will also be indicated briefly as a catheter.

Inside the outer tubular structure 21, an inner tubular structure 23 is arranged. In the embodiment illustrated in FIG. 3, the inner tubular structure 23 substantially consists of a side wall of a small diameter tube, terminating with a terminal end closed by a closing element 24.

In some embodiments, the outer tubular structure or catheter 21 and the inner tubular structure 23 may have a circular cross-section, as shown in detail in the transversal cross-section of FIG. 4.

The outer tubular structure or catheter 21 comprises a tubular wall with an outer surface 21.1 and an inner surface 21.2. Similarly, the inner tubular structure 23 comprises a side wall with an outer surface 23.1 and an inner surface 23.2. The inner surface 23.2 defines an inner volume of the inner tubular structure 21. Between the inner surface 21.2 of the outer tubular structure 21 and the inner surface 23.1 of the inner tubular structure 23 a gap 25 having an annular cross-section is defined.

When assembled, a light guide or optical guide 27 is inserted into the inner tubular structure 23 and forms an element that conveys the electromagnetic radiation towards the terminal end of the outer tubular structure 21. As can be seen in detail in the cross-section of FIG. 4, the light guide 27 is approximately coaxial with the inner tubular structure 23 and a gap 29 is formed between the inner surface 23.2 and the light guide 27. The light guide is optically connected to a laser source (described below), that generates a laser beam of suitable wavelength and power, for the thermal ablation treatment. Embodiments of the light guide 27 will be described in greater detail below.

In the embodiment illustrated in FIGS. 3 and 4 the tubular wall of the inner tubular structure 23 comprises a plurality of lateral openings or apertures 31, formed in the side wall of the inner tubular structure 23. The lateral openings or apertures 31 put the gap 25 into fluid communication with the inner volume of the inner tubular structure 23 and more specifically with the gap 29. In this way, a coolant entering the gap 25 can reach the terminal area of the outer tubular structure 21 and of the inner tubular structure 23 and enter inside the inner tubular structure 23 before returning towards the apparatus with which the device 1 is interfaced. Circulation of the coolant may also be reversed, with feeding through the gap 29 and return through the gap 25.

Although in theory it is possible to provide a single lateral opening 31, for a better flow of the coolant it is advantageous to provide two or preferably at least three lateral openings or apertures 31. Advantageously, in some embodiments the lateral openings 31 are arranged angularly staggered with respect to each other around a longitudinal axis A-A of the inner tubular structure 23 and outer tubular structure 21, substantially coaxial with each other. In some embodiments the angular offset may be constant. For example, if three lateral openings 31 are envisaged, they may be arranged staggered by 120° with respect to each other. Furthermore, in advantageous embodiments the lateral openings 31 are distributed along the axis A-A of the outer tubular structure 21 and of the inner tubular structure 23, that is to say they are spaced with respect to each other along the longitudinal development of the device 1.

The lateral apertures or openings 31 may have any suitable shape, for example circular or elliptical.

It has been found that, by means of the lateral openings 31, better flow of the coolant, in particular a coolant liquid, is achieved between the gap 25 and the gap 29 or vice versa. The flow obtained through the lateral openings 31 tends to be laminar, preventing or limiting in that way the formation of vortexes in the tip of the device. Thanks to the laminar nature of the flow, head losses are lower than in the devices according to the prior art, in which the fluid connection between the outer gap and the inner gap occurs through the open end of the inner tubular structure. By providing lateral apertures or openings 31 better circulation of the coolant is achieved and therefore greater flow at the same coolant thrust, i.e. coolant pressure.

Figure 5:
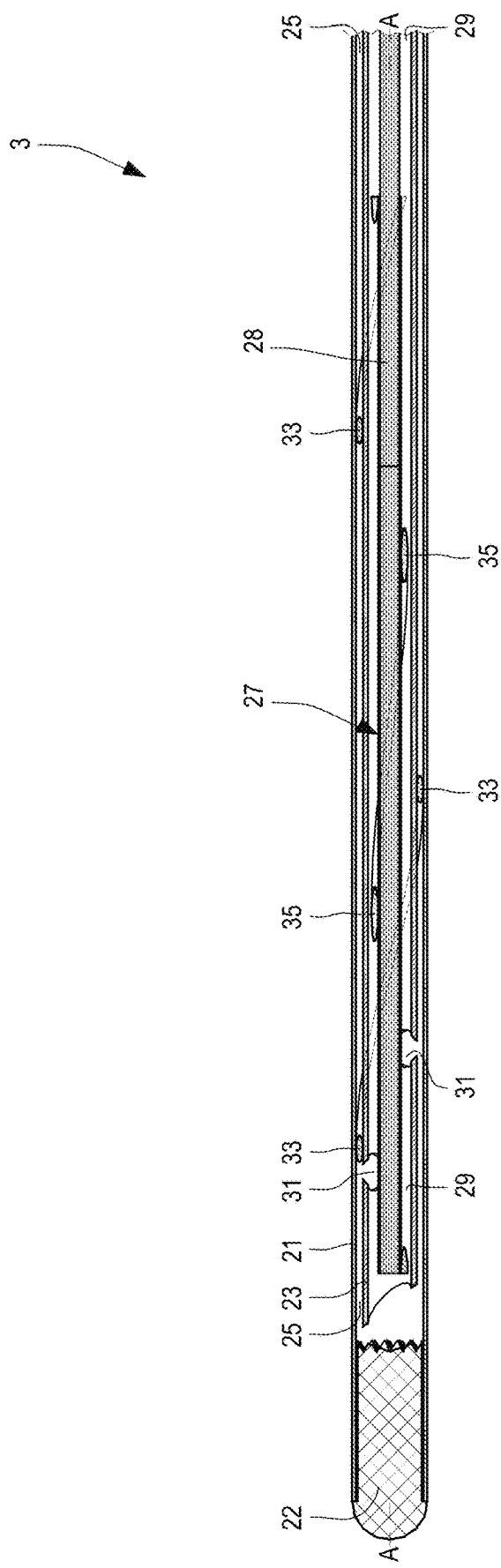
FIG. 5 a cross-section according to a plane containing the longitudinal axis of a catheter in a different embodiment.

This improvement in the coolant flow is obtained both with a configuration of the type illustrated in FIG. 3, where the terminal end of the inner tubular structure 23 is closed by the closing element 24 and, although to a lesser extent, with a structure of the type illustrated in FIG. 5. This figure shows a device substantially the same as that shown in FIG. 3, but differing from the latter substantially only in that the inner tubular structure 23 is open frontally, rather than closed by the closing element 24. To improve the flow conditions, the terminal end of the inner tubular structure 23 is obliquely cut i.e. an oblique cut with respect to the longitudinal axis A-A.

Figure 6:
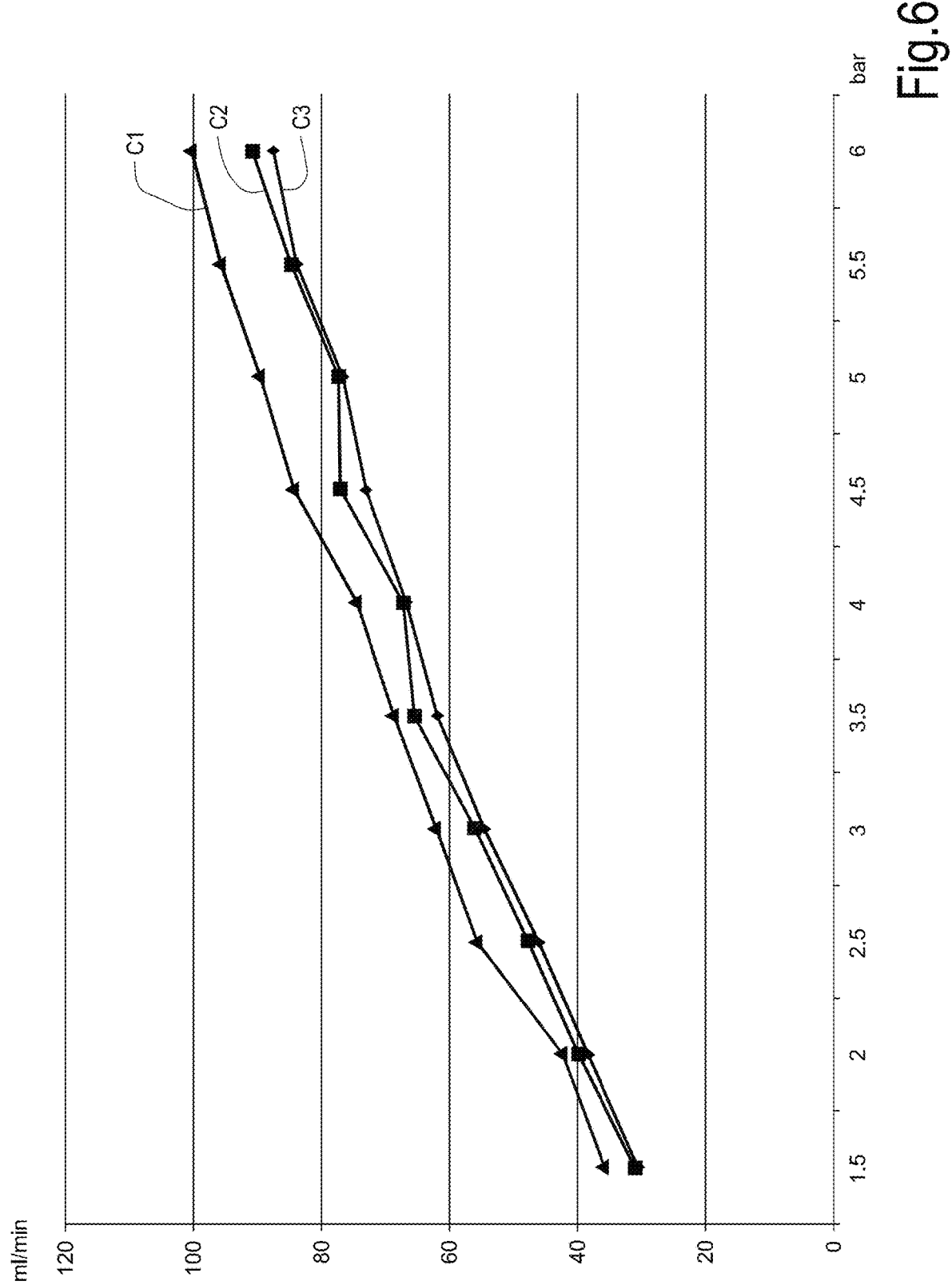
FIG. 6 a diagram illustrating the coolant flow rate according to the supply pressure.

The increase in coolant flow enables the device to deliver more power and obtain larger ablation volumes, allowing the treatment of larger sized tumors even in an advanced state. FIG. 6 shows a diagram that indicates the flow rate in ml/min of a coolant according to the pressure applied to achieve its circulation inside the device 1. In the diagram of FIG. 6 3 curves are shown, marked C1, C2, C3, obtained experimentally. Curve C1 is obtained with a device of the type illustrated in FIG. 3, while curve C3 and curve C2 represent the flow rates for devices according the prior art, without lateral openings or apertures formed on the wall of the inner tubular structure and in which connection between the gap 25 and the gap 29 is obtained solely in at the frontal opening, i.e. through the terminal opening of the inner tubular structure 23. Curves C2 and C3 have been obtained with an inner tubular structure terminating with an inclined edge, formed by an oblique cut, and with an edge at right angles to the longitudinal axis, respectively.

The embodiment according to the invention shows a substantial increase in the flow rate of approximately 15-20% with respect to the configurations according to the prior art, at the same pressure.

In order to achieve efficient cooling, it is advisable for the flow of coolant to be as even as possible within the gaps formed by the outer tubular structure 21, the inner tubular structure 23 and the light guide 27. It is also advisable not to have areas with a reduced flow rate in the distal part of the device, that is to say in proximity to the lateral openings or apertures 31. On the other hand, to achieve uniform irradiation of the surrounding tissues, into which the catheter 21 is inserted, it is advisable that the light guide 27, the inner tubular structure 23 and the outer tubular structure 21 be as concentric as possible with respect to each other. The presence of spacers traditionally formed by extrusion, inside the gaps 25 and 29, reduces the working transversal cross-section for the flow, increasing as a consequence the head loss and reducing the flow rate. Furthermore, the spacers according to the prior art make the flow of coolant non-uniform, with a consequent lack of uniformity in the cooling effect.

According to advantageous embodiments described herein, in order to solve or alleviate these problems, spacers of an innovative shape are used. With reference to FIGS. 3 and 4, a first spacer 33 is arranged in the gap 25 between the outer tubular structure 21 and the inner tubular structure 23. This spacer has the form of an element with a linear development, that is to say a threadlike form, that winds helically around the longitudinal axis A-A of the inner tubular structure 23 and the outer tubular structure 21. The helical shape of the first spacer 33 is visible in detail in FIG. 3. The helically developing spacer 33 may have a circular cross-section, as shown in FIG. 4. In other embodiments the first spacer 33 may have a transversal cross-section of a different shape, for example elliptical. Regular or irregular polygonal shapes cannot be excluded for the transversal cross-section of said spacer 33, that may be dictated by the need to improve the flow conditions. In practical embodiments the first spacer 33 is manufactured as component which is physically separate with respect to both the inner tubular structure 23, and to the outer tubular structure 21, rather than being obtained by extrusion as a single piece with one or the other of said tubular structures. This allows the first spacer 33 to be arranged helically at the required pitch around the longitudinal axis A-A.

The first spacer 33, with a helical development, allows the outer tubular structure 21 and the inner tubular structure 23 to be maintained coaxial with each other, without representing an excessive obstacle to circulation of the coolant inside the gap 25. In effect, the reduction in useful cross-section for the flow of coolant corresponds to the area of the transversal cross-section of the individual spacer 33. The helical arrangement allows the inner tubular structure 23 to be maintained coaxial with the outer tubular structure 21 with a single spacer, whereas the solution according to the prior art, with spacers formed as a single piece by extrusion with the outer or inner tubular structure, would require the use of at least three spacers staggered at an angle of 120° with respect to the longitudinal axis of the outer tubular structure and of the inner tubular structure.

The first spacer 33 allows the inner tubular structure 23 and the outer tubular structure 21 to be maintained concentric with each other. To improve the efficiency of the device, it is advisable also to maintain the inner tubular structure 23 and the light guide 27 concentric. In advantageous embodiments, to that end, referring again to FIGS. 3 and 4, a second spacer 35 can be arranged in the gap 29. The second spacer 35 may have substantially the same form as the first spacer 33, that is to say it may consist of an elongated linear element, that is to say a threadlike element, for example with a circular transversal cross-section. The second spacer 35 may be arranged helically around the longitudinal axis A-A, as shown in the longitudinal cross-section of FIG. 3. The spacer 35 allows the light guide 27 to be maintained substantially coaxial with the inner tubular structure 23, without significantly hindering the flow of coolant in the gap 29.

Using linear, helically wound elements as spacers, instead of straight spacers extruded together with the tubular structure, also gives the advantage of being able to provide those spacers only in the terminal area of the outer tubular structure 21 and of the inner tubular structure 23, leaving completely free the passage section defined by the gaps 25 and 29 in the proximal area of the tubular structures 21, 23, as can be seen in detail in the cross-section of FIG. 3.

Figure 7:
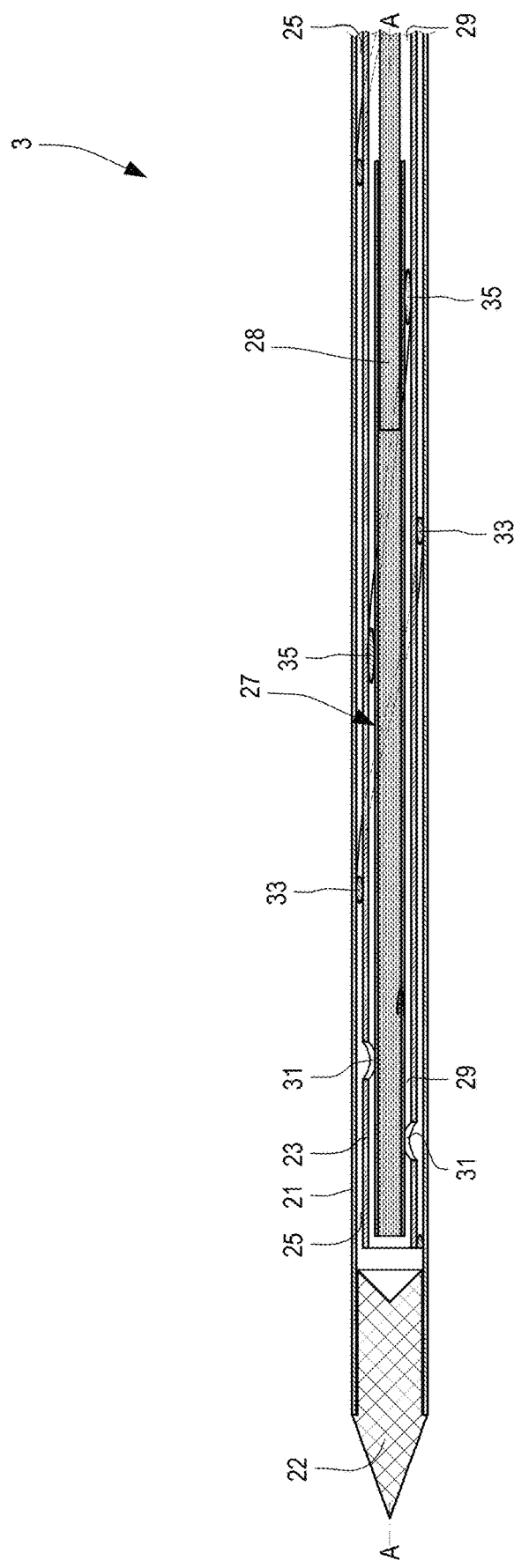
FIG. 7 a cross-section according to a plane containing the longitudinal axis of a catheter in a further embodiment.
Figure 8:
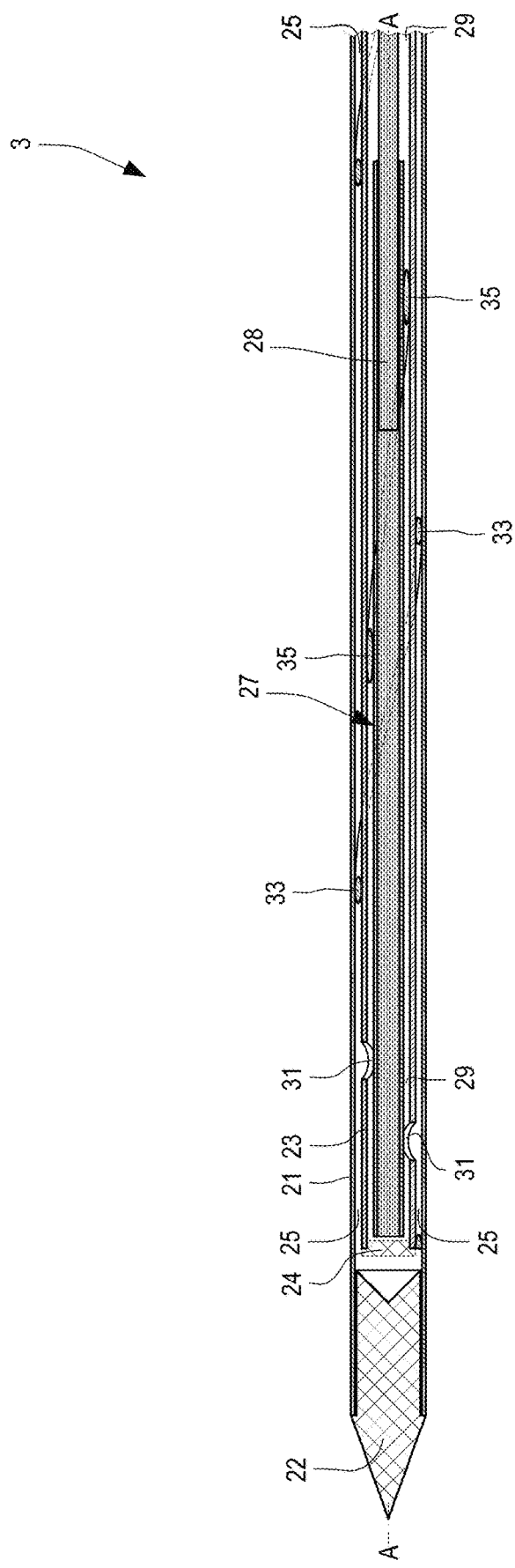
FIG. 8 a cross-section according to a plane containing the longitudinal axis of a catheter in yet another embodiment.

In the embodiment of FIGS. 3 and 5 the terminal end of the inner tubular structure 21 is closed by a closing element 22, with a nose-cone shape, that is to say with a rounded outer end. As will be clarified in greater detail in the following, the closing element 22 can be made with various optical properties, for example it can be transparent, diffusing or reflecting at the wavelength of the electromagnetic radiation carried by the light guide 27. In alternative embodiments the closing end 22 of the outer tubular structure 21 may have a different shape, for example a conical or pyramidal shape, as illustrated as an example in the embodiments of FIGS. 7 and 8. The embodiment of FIGS. 7 and 8 are for the remainder substantially similar to the embodiments of FIGS. 3 and 5 and are therefore not described in greater detail. The same reference numbers are used to indicate corresponding elements in the various embodiments. The embodiment of FIG. 7 has an inner tubular structure 23 with an open distal or terminal end, while the embodiment of FIG. 8 has an inner tubular structure 23 with a terminal end which is closed by a closing element 24.

In the embodiments illustrated in FIGS. 3 and 5 the light guide 27 comprises an optical fiber 28 that extends inside the inner tubular structure 23 until it is closely adjacent to its distal end. The terminal part of the optical fiber 28 can be machined so as to be diffusing, that is to say to allow the optical radiation carried by the light guide 27 to flow out through the side wall of the optical fiber. The optical radiation that diffuses from the side wall of the terminal portion of the optical fiber 28 can cross the inner tubular structure 23 and the outer tubular structure 21 so as to diffuse into the tissue into which the catheter formed by the outer tubular structure 21 has been inserted. For that purpose at least a part of the inner tubular structure 23 and of the outer tubular structure 21 are made in a material that is transparent or diffusing at the wavelength of the electromagnetic radiation carried along the light guide 27.

In other embodiments, the optical fiber 28 may have a shorter longitudinal extension and may terminate at a certain distance from the distal or terminal end of the inner tubular structure 23. In the embodiments of FIGS. 7 and 8, the light guide 27 comprises an optical fiber 28 and a diffuser 30, which extends from the tip 28P of the optical fiber towards the terminal end of the inner tubular structure 23. The diffuser 30 is made in such a way that the electromagnetic radiation transmitted by the light guide 27 propagates from the lateral surface of the diffuser 30. In this case also at least a part of the inner tubular structure 23 and of the outer tubular structure 21 are made in materials that are transparent or diffusing at the wavelength of the electromagnetic radiation carried along the light guide 27.

Specific embodiments of the diffuser 28 will be described below with reference to FIGS. 19, 20, 21.

Figure 9:
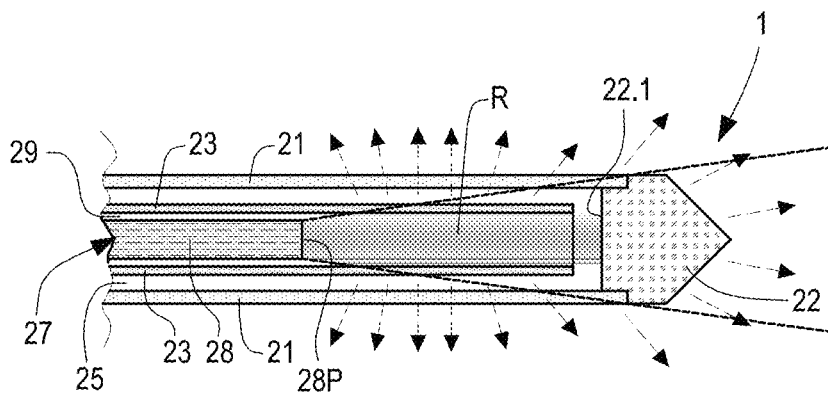
FIGS. 9, 10, 11 embodiments of the terminal part of the catheter and the components it contains.
Figure 10:
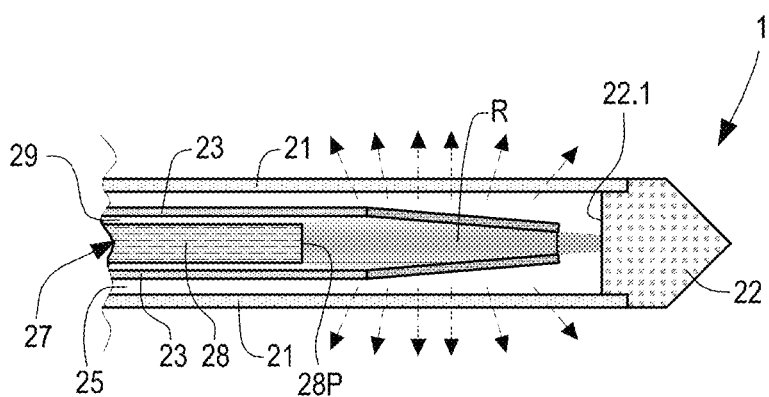
Figure 11:
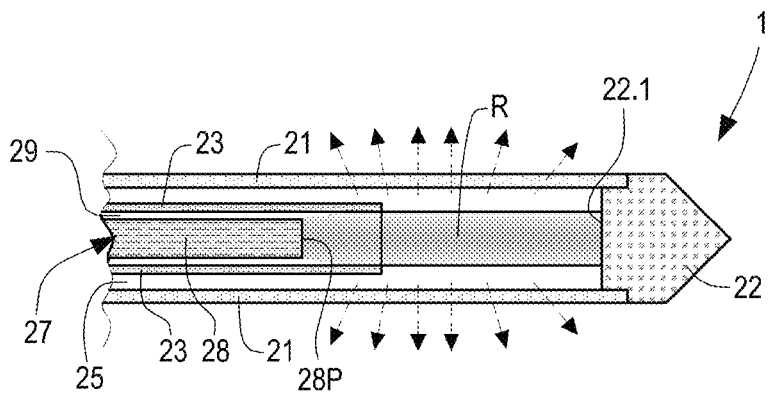

In other embodiments, the light guide 27 may terminate at a certain distance from the terminal end of the inner tubular structure 23. For example, the light guide 27 may comprise the optical fiber 28 and may not have a diffuser 30, with a terminal end of the optical fiber 28 located at a distance from the terminal end of the inner tubular structure 23 equal to a multiple of the diameter of the inner tubular structure 23. Exemplary embodiments of a device 1 of this type are illustrated in FIGS. 9, 10, 11. In these embodiments the electromagnetic radiation R is mainly emitted from the tip of the optical fiber 28, which remains fully housed in the inner tubular structure 23. The tip of the optical fiber 28 may be suitably shaped, to emit a beam of electromagnetic radiation, and more specifically a beam of laser radiation, of a suitable form, for example diverging. The materials of which the inner tubular structure 23 and the outer tubular structure 21 are made are selected so as to achieve diffusion of the electromagnetic radiation towards the outside of the outer tubular structure 21, to irradiate the surrounding tissue, into which the catheter formed by the outer tubular structure 21 is inserted.

For that purpose, in some embodiments at least the terminal part of the inner tubular structure 23 may be made of a material that is transparent to the electromagnetic radiation used, whereas at least the terminal portion of the outer tubular structure 21 is made of material that is diffusing at that wavelength. In other embodiments, the terminal portion of the inner tubular structure 23 may also be made of a diffusing material, instead of one that is transparent at the wavelength used. In yet other embodiments, the inner tubular structure 23 may be made, at least in its terminal portion, of a material that is diffusing at the electromagnetic radiation used, whereas at least the terminal portion of the outer tubular structure 21 may be made of a material that is transparent to that electromagnetic radiation. In general terms, at least one of the outer tubular structure 21 and the inner tubular structure 23 is made of a diffusing material, while the other may be made of a material that is transparent to the electromagnetic radiation used, or both may be made of diffusing material.

In FIG. 9 the terminal part of the inner tubular structure 23 is made of diffusing material and the beam of electromagnetic radiation, for example a laser beam, that comes out from the distal end of the optical fiber 28 diffuses through the inner tubular structure 23 towards the outer tubular structure 21 and through the latter, which is made of transparent material. In the embodiment illustrated in FIG. 9, the terminal element 22 closing the outer tubular structure 21 is made of material that is transparent or diffusing to the electromagnetic radiation used, so that said radiation can also diffuse frontally.

In the embodiment of FIG. 10 the terminal portion of the inner tubular structure 23 is tapered, so as to increase the portion of electromagnetic radiation that is incident on the inner surface of the inner tubular structure 23 and facilitate the outwards diffusion thereof, i.e. the diffusion toward the outer tubular structure 21. The latter may be made transparent or diffusing. In the embodiment of FIG. 10 the closing element 22 of the terminal end of the outer tubular structure 21 is reflecting, and has a surface 22.1 facing towards the inside of the outer tubular structure 21, so that the electromagnetic radiation exiting frontally from the inner tubular structure 23 is reflected by the surface 22.1 towards the inside of the outer tubular structure 21. The option is not ruled out to provide the embodiment of FIG. 10 with a terminal closing element 22 that is transparent or preferably diffusing as envisaged in the embodiment of FIG. 9.

FIG. 11 shows yet another embodiment, in which the inner tubular structure 23 may be opaque to the radiation carried through the light guide 27. The beam of electromagnetic radiation comes out of the distal or terminal end of the inner tubular structure 23 and is diffused through the diffusing material of which at least the distal part of the outer tubular structure 21 is made. The terminal element 22 closing the outer tubular structure 21 is reflecting, as in the embodiment of FIG. 10. However the option of providing said closing element 22 in transparent or preferably diffusing material, as envisaged in the embodiment of FIG. 9, is not excluded.

In the various embodiments the beam that comes out of the tip 28P of the optical fiber is normally diverging. This occurs particularly when the tip 28P of the optical fiber 28 is flat. The divergence is defined by the numerical opening NA of the optical fiber 28. Typical divergence values are 0.22 mRad, 0.27 mRad, 0.37 mRad. However, the option of creating different values during the manufacturing phase, by varying the refractive index of the cladding and the core of the optical fiber 28, is not excluded.

The divergence of the laser beam coming from the optical fiber 28 may be used to hit a diffusing structure in the immediate vicinity of the tip, typically the inner tubular structure 23 or the outer tubular structure 21, and obtain a strong lateral emission.

Moreover, the tip 28P of the optical fiber 28 may be machined to achieve increased divergence of the beam. In particular, for example, a conical geometry of the tip with polished or rough surfaces can act on the optical beam coming out, obtaining an emission with increased divergence. The divergence obtained according to the angle at the vertex of the tip can be calculated by applying the Snell law to the fiber-air or fiber-liquid interface if the optical fiber is submerged in a liquid, and the direction of the refracted light component is assessed.

Different approaches can be used to obtain a material that is diffusing at the wavelength of the electromagnetic radiation conveyed along the light guide 27.

In some embodiments, diffusion of the electromagnetic radiation is achieved by adding suitable colorants or powders in the base material from which the outer tubular structure 21 and/or the inner tubular structure 23 is formed, by extrusion. In other embodiments, the material that renders the inner tubular structure 23 or the outer tubular structure 21 can be applied on the surface after extrusion. The diffusing properties can be envisaged only in the distal part of the relevant tubular structure (inner 23 and outer 21) or can involve the entire tubular structure.

To obtain the diffusing capacity of the inner tubular structure 23 and/or the outer 21 it is also possible to use other methods, for example mechanical abrasion machining or chemical etching. These methods achieve roughening of the surface of the tubular structure 21 and/or 23 which results in a localized change in the light guiding conditions according to Snell's law.

In yet other embodiments, to obtain diffusing property it is possible to create the inner tubular structure 23 with undulations on one plane or on two planes at right angles to each other, essentially to create a helical shape in the inner tubular structure 23. The undulations in the inner tubular structure 23 cause the electromagnetic radiation to hit the walls of the inner tubular structure 23, generating diffusion and/or refraction-reflection effects. In some embodiments, the outer tubular structure 21 may also be given an undulating shape, if this does not hinder insertion of the device into the tissue to be treated.

In combination with or as an alternative to the above described means to achieve diffusion of the electromagnetic radiation towards the outside of the outer tubular structure 21, it is possible to use a coolant circulating in the gaps 25 and 29, which contains a suspension of diffusing particles or powders. These powders may have dimensions between, for example, approximately 10 nm and approximately 100 micrometers. The diffusing particles or powders can be selected in such a way as to have a reduced absorption of the electromagnetic radiation used. For example, it is possible to use particles of hydroxyl apatite, TiO, $TiO_2$, $Al_2O_3$. In addition, it is possible to use, for example, Barium sulphate ($BaSO_4$) which also has radio-opacity properties and allows viewing of the device using X-ray imaging techniques. The option of using other diffusing and radio-opaque substances is not to be excluded. The optional addition of iodine in the liquid makes it possible to obtain a diffusing and radio-opaque liquid for detection of the device in X-ray or tomographic (TC) images.

In other embodiments, liquid diffusing particles can be used in place of the solid diffusing particles. For example, a coolant can be used in which a certain amount of a second liquid has been mixed, that is non-miscible with the coolant and has diffusing properties.

The various technical solutions described above to obtain diffusion of the electromagnetic radiation outside the outer tubular structure 21 can be combined with each other and/or with the use of optical fibers that have been machined so as to be diffusing at least in the distal portion, or can be combined with optical diffusers located axially in front of the optical fiber itself.

In the embodiments illustrated in FIGS. 9, 10 and 11 the closing element 22 located at the terminal end of the outer tubular structure 21 has a partially cylindrical and partially conical or pyramidal form. However, different forms are also possible for said closing element 22. FIG. 12 illustrates four different possible geometric forms for the closing element 22. Each of these geometric forms can be used to create a closing element 22 that is diffusing or reflecting. In FIGS. 12A, 12C, 12E, 12G the closing element 22 is made of diffusing material, so that the electromagnetic radiation coming out of the light guide 27 is also diffused frontally into the tissue, in which the catheter formed by the outer tubular structure 21 is inserted. In the embodiments of FIGS. 12B, 12D, 12F, 12H the closing element 22 has a reflecting inner surface 21.1, so that the electromagnetic radiation incident on it is reflected backwards.

The various configurations of the closing element 22 differ from each other both as regards the portion of surface facing towards the inside of the outer tubular structure 21, and as regards the surface facing towards the outside of the outer tubular structure 21. For example, in FIGS. 12A, 12B the inner surface 22.1 is a convex pyramid or cone, whereas in FIGS. 12C, 12D said inner surface is flat. Vice versa, the outer surface is a truncated pyramid or truncated cone in FIGS. 12A, 12B and semi-spherical in FIGS. 12C, 12D. In the following figures the inner surface is concave, and the outer surface is partially cylindrical and partially spherical, conical or pyramidal. It must be understood that the different forms of the inner and outer surfaces illustrated in FIG. 12 may be combined in manners other than those illustrated.

In some embodiments, the outer tubular structure 21 may have a flexible portion, formed for example by an elastic membrane. This material allows dilation under the effect of the pressure from the coolant. The elastically deformable portion of the outer tubular structure 21, when expanded, causes compression of the surrounding tissues and therefore an increase in the surface irradiated by the electromagnetic radiation propagated through the light guide 27.

Figure 13:
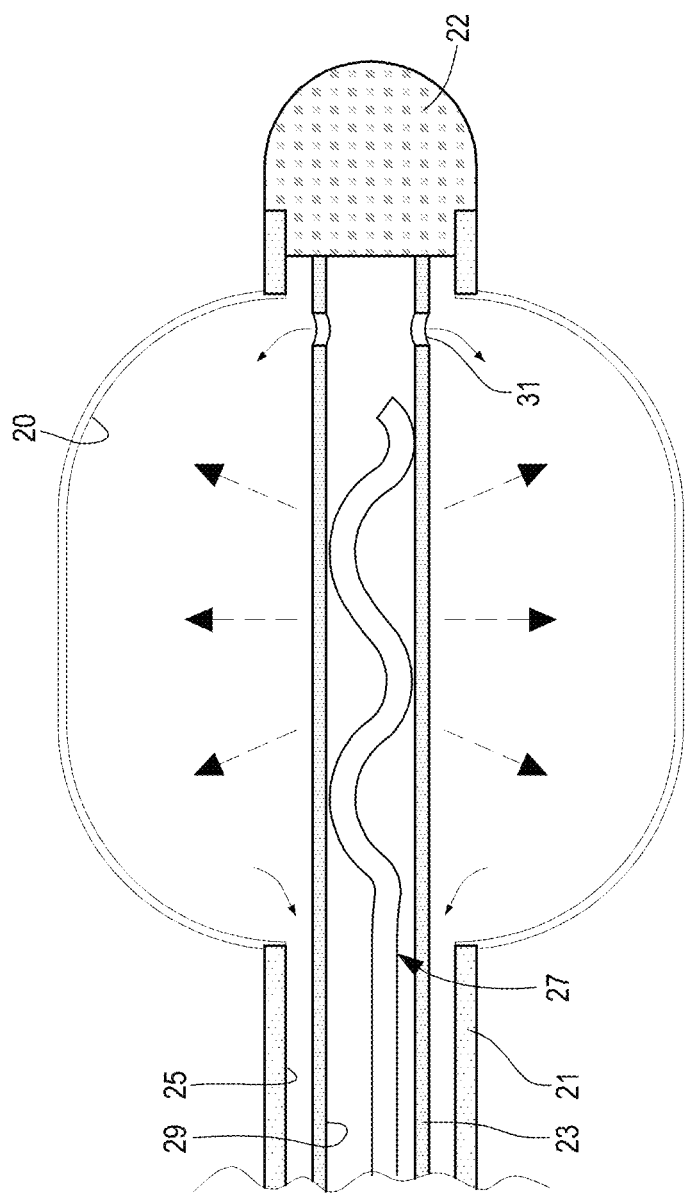
FIG. 13 an embodiment of a catheter with an inflatable element.

An embodiment in which the outer tubular structure 21 is partially formed by an elastically deformable material is schematically shown in FIG. 13. In the vicinity of the distal end the outer tubular structure 21 has a portion formed by an elastically deformable membrane 20, which in FIG. 13 is shown as expanded by the effect of pressure from a coolant circulating in the gap 29 and in the gap 25. In this embodiment, the flow of coolant is from the inside of the inner tubular structure 23 towards the inside of the outer tubular structure 21. The lateral openings 31 that put the gap 29 in fluid connection with the gap 25 are advantageously found in correspondence with the portion of the outer tubular structure 21 formed from the elastically deformable material 20, so that when the coolant is pumped into the gap 29 it comes out of the lateral openings 33 and inflates the membrane 20 to form a dilated balloon, before flowing into and along the gap 25. As an example, in the embodiment illustrated in FIG. 13 the light guide 27 is shown with a helical form, for the purposes that will be clarified in greater detail below with reference to further embodiments. In other embodiments the light guide 27 may be straight. The inner tubular structure 23 may be transparent or diffusing at the wavelength of the electromagnetic radiation used, so as to allow the electromagnetic radiation to come out through the volume of the balloon formed by the membrane 20, which in turn may be diffusing or transparent at the wavelength of the electromagnetic radiation used. Any particles suspended in the coolant may facilitate or render more uniform the diffusion of the electromagnetic radiation.

Figure 14:
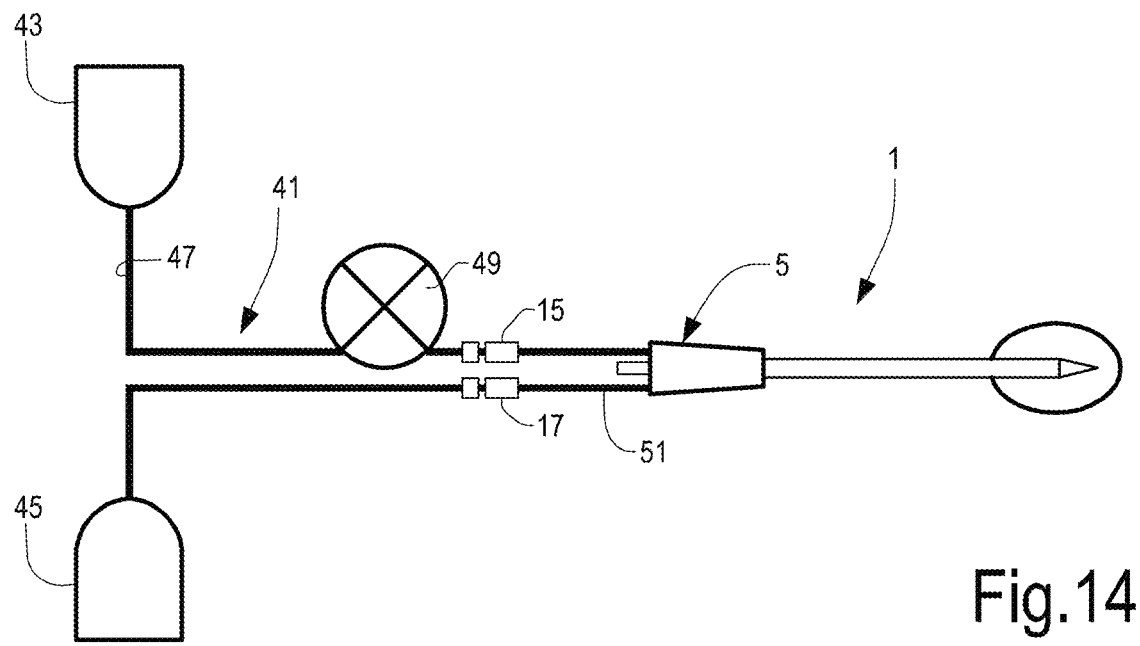
FIGS. 14 and 15 diagrams of a cooling circuit of an apparatus using the device described herein.

The coolant that is made to circulate in the device 1 may be a disposable fluid, or it may be made to circulate in a closed circuit. FIG. 14 is a diagrammatic illustration of a cooling circuit connected to the device 1, with a configuration in which the coolant is disposable. The coolant may be, for example, a saline solution or any other biocompatible fluid, so that any dispersion from device 1 toward the treated tissues causes no harm to the patient. In the solution diagrammatically illustrated in FIG. 14 the cooling circuit, indicated as a whole with 41, comprises a first tank 43 containing a fresh coolant and a second tank 45 containing used coolant. By means of a pipe 47 the first tank 43 is connected to the channel 7 or to the channel 9 of the connection element 5 of device 1 (see FIGS. 1 and 2). A pump, for example a peristaltic pump, is indicated with 49, which causes the coolant to circulate in the cooling circuit 41. The used coolant coming from device 1 is carried into the tank 45 via a pipe 51.

The volume of coolant contained in the first tank 43 may be sufficient to guarantee cooling during the entire treatment cycle, so as to avoid the need to replace the tank 43 during the operation.

Figure 15:
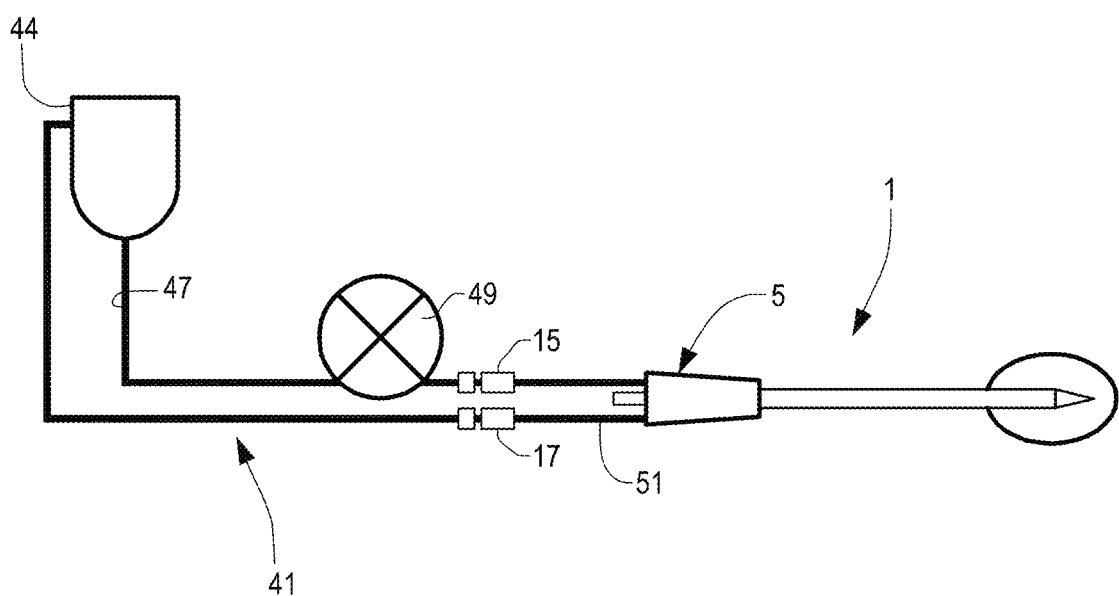

In the embodiment schematically illustrated in FIG. 15, the cooling circuit, again labeled 41, is a closed circuit, so that the coolant circulated by means of the pump 49 is taken from the tank 44 and returned to it. The tank 44 may be suitably refrigerated, so as to maintain the coolant at a suitable temperature to carry out its function of removing heat from the treatment area. The tank 44 may also be formed in reality by the internal volume of a pipe forming part of a heat exchanger.

Figure 16:
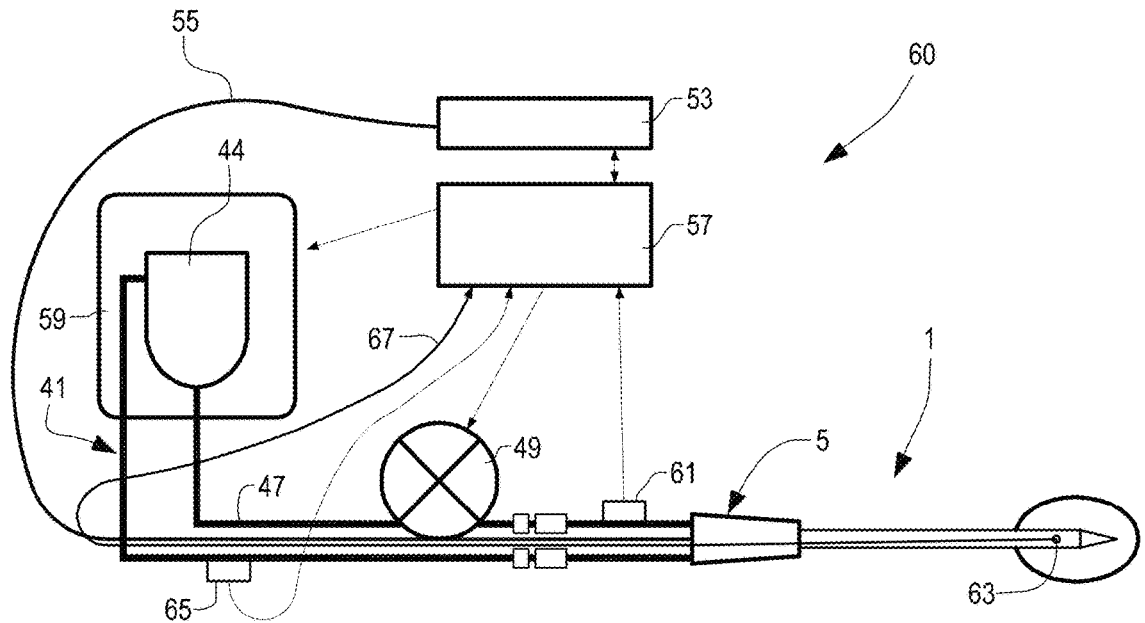
FIGS. 16 and 17 diagrams of apparatuses according to the invention in two embodiments.

FIG. 16 is a diagrammatic illustration of an apparatus 60 that uses the device 1 in one of the embodiments described above. In the diagram of FIG. 16 the cooling circuit 41 is a closed circuit. Indicated by 53 is a laser source that emits a laser radiation that is conveyed by means of an optical fiber 55 to the device 1. The optical fiber 55 can be connected to the light guide 27 of the device 1 by means of the connection element 5, through the connector 19 (FIG. 1). The optical fiber 55 may optionally be an extension of the optical fiber 28 described above.

Indicated by 57 is a control unit, that may be connected to the laser source 53 to control emission of the laser radiation, to the pump 49 in the cooling circuit 41, and to a cooling device 59 to remove coolant heat from the cooling circuit 41. The control unit 57 may also be functionally connected to further sensors in the apparatus 60. For example, a pressure sensor 61 may be provided, which detects the pressure in the delivery branch of the cooling circuit 41, that is to say in the pipe 47, downstream of pump 49. At the distal end of device 1, that is to say preferably inside the outer tubular structure 21 and adjacent to its terminal end, a temperature sensor 63 may be positioned, to keep under control the temperature in the catheter formed by the outer tubular structure 21 and therefore indirectly in the surrounding tissue, into which the catheter has been inserted. In some embodiments a flow meter 65 may also be provided, which measures the flow rate of coolant circulating in the cooling circuit 41.

The sensors 61, 63, 65 allow control of the operation of all the apparatus 60 and of the device 1 that is interfaced with it. The electrical connection between the central unit 57 and the temperature sensor 63 may be obtained using a cable 67 that passes through the channel 11 in the connection element 5 (FIG. 2).

Figure 17:
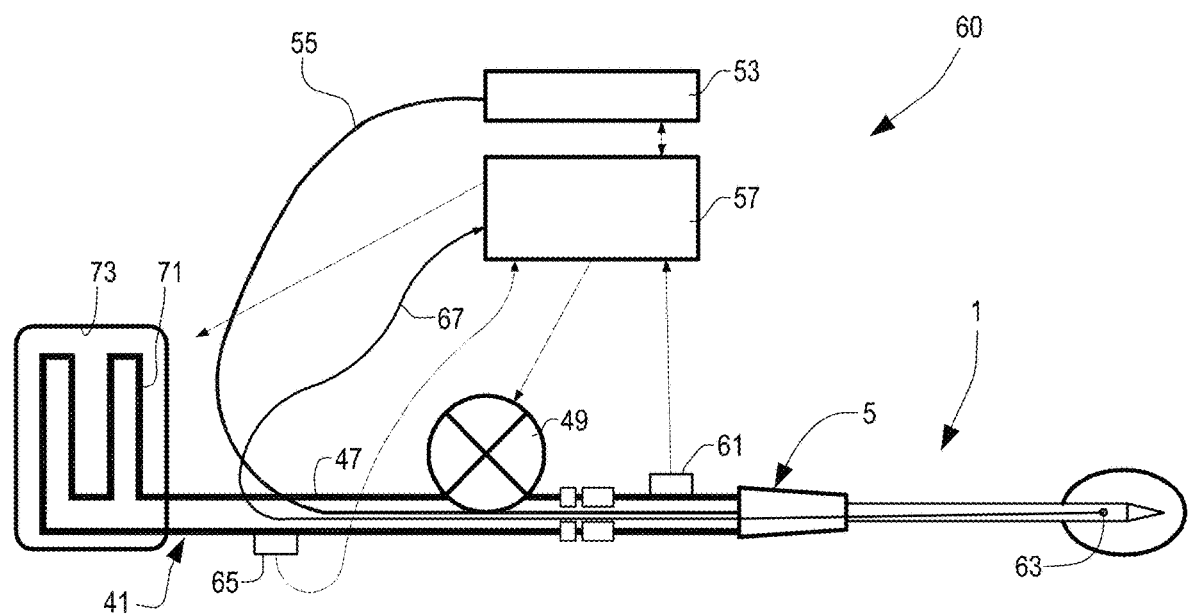

FIG. 17 shows an apparatus 60 similar to the one described with reference to FIG. 16. The same numbers indicate parts that are the same as or correspond to those already described with reference to FIG. 16. In the embodiment of FIG. 17, instead of a tank for the coolant, a pipe is provided, indicated by 71, forming a heat exchanger and with an overall internal volume sufficient to contain a suitable amount of coolant. The pipe 71 may be located at least partially inside a cooling system 73, for example comprising a Peltier cell, to cool the coolant circulating in the cooling circuit.

The use of a temperature sensor associated with the device 1 may allow monitoring the treatment carried out using that device. The temperature sensor may provide information to the control unit 57, in particular information on the temperature of the coolant and therefore, indirectly, on the temperature that is developed in the surrounding tissues during treatment. This temperature depends on the tissue and is a function of its absorption coefficient, scattering, the wavelength of the radiation used, the power emitted, and the flow rate of the coolant, as well as the temperature of the latter.

The control unit 57 may act on the power delivered by the source 53, on the flow rate of the coolant and on its temperature, to control the temperature in the surrounding tissues.

The temperature sensor 63 may also be used to measure the temperature of the tissue directly. For that purpose, it is sufficient to stop emission of the laser radiation by the source 53 and circulation of the coolant by the pump 49. Within a few seconds (4-5 seconds) the temperature of the coolant that is inside the outer tubular structure 21 reaches the temperature of the surrounding tissue and is measured directly by the temperature sensor 63.

By controlling the parameters described above it is also possible to stop delivery of power by the laser source 53, while maintaining the circulation of coolant by means of the pump 49 active, when a critical temperature is reached.

The flow meter 65 on the return branch of the cooling circuit 41 and the pressure sensor 61 on the delivery branch of the cooling circuit 41 identify any anomalies in flow that are incompatible with proper operation of the device. For example, it is possible to detect any leakages of coolant. It is also possible to provide two flow meters, one on the delivery branch and one on the return branch.

In some embodiments the control unit 57 can act on the cooling system 59, 73, which adjusts the temperature of the coolant, for example to obtain temperature control of the coolant, increasing the efficiency of tissue cooling.

The coolant used may be a liquid or a gas. As mentioned above, in the case of a liquid coolant it is possible to use a saline solution, consisting of water and NaCl 0.9% or other suitable concentrations. As a gas coolant it is possible to use nitrogen, carbon dioxide or another suitable gas.

As indicated above, the light guide 27 may comprise an optical fiber 28 that extends up to the terminal end of the inner tubular structure 23. The optical fiber 28 may have a surface machining in its terminal area, that is to say close to the terminal end of the inner tubular structure 23 and of the outer tubular structure 21, that facilitates lateral emission by diffusion of the electromagnetic radiation carried by the optical fiber 28 itself. In other embodiments, the optical fiber 28 may be associated with an optical diffuser 30 (see FIGS. 7 and 8). The optical diffuser 30 may have a form or a surface machining, or it may be made of a suitable material, to facilitate lateral diffusion of the electromagnetic radiation.

Figure 18:
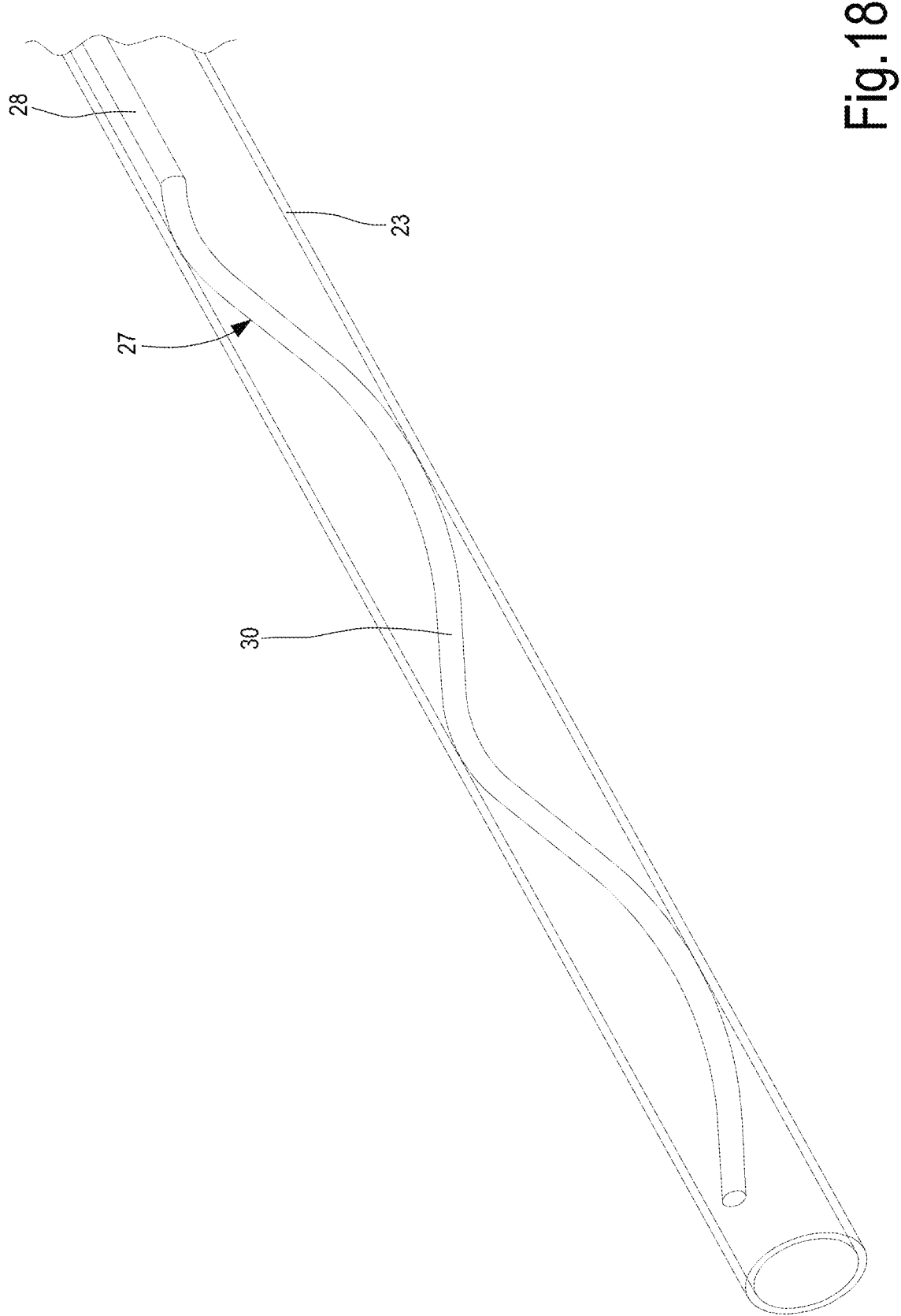
FIG. 18 an axonometric view of a terminal portion of a light guide inserted in an inner tubular structure in an alternative embodiment.

In particularly advantageous embodiments, the optical diffuser 30 has an undulating form, on a plane and on two planes at right angles, for example taking on a helical form, as illustrated diagrammatically in FIG. 18. This figure only shows the inner tubular structure 23, the terminal portion of the optical fiber 28 and the diffuser 30. The latter has a helical extension around a longitudinal geometric axis of the inner tubular structure 23. The undulating form of the diffuser 30 facilitates propagation of the electromagnetic radiation to the outside.

Figure 22A:
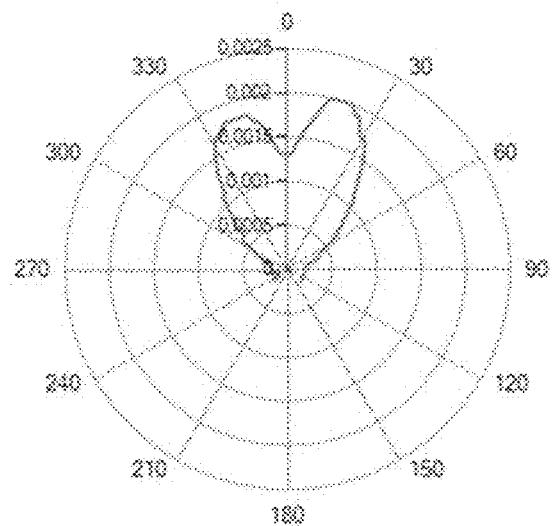
FIGS. 22A-22I emission diagrams for the light guide diffuser in various embodiments.
Figure 22B:
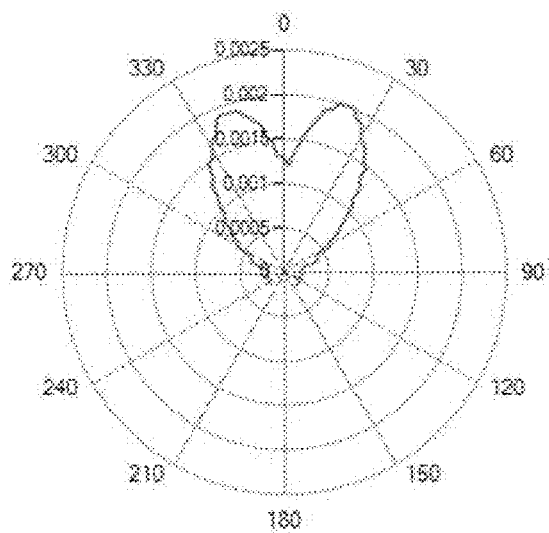
Figure 22C:
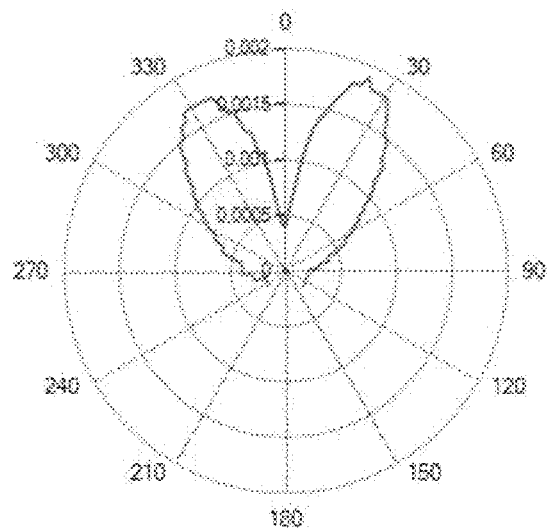
Figure 22D:
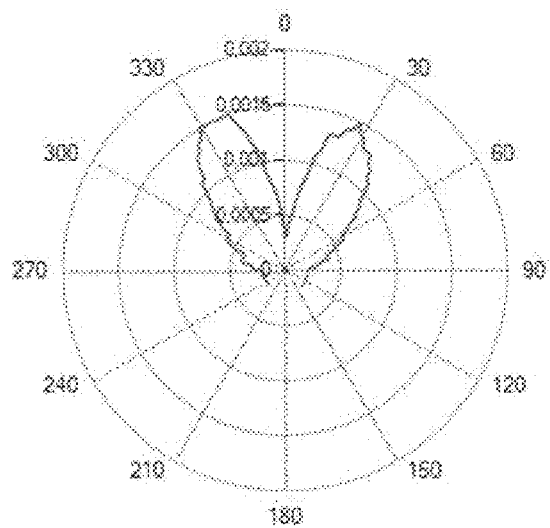
Figure 22E:
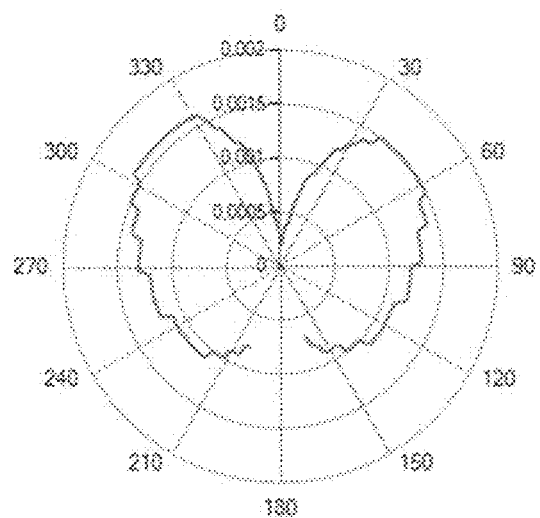
Figure 22F:
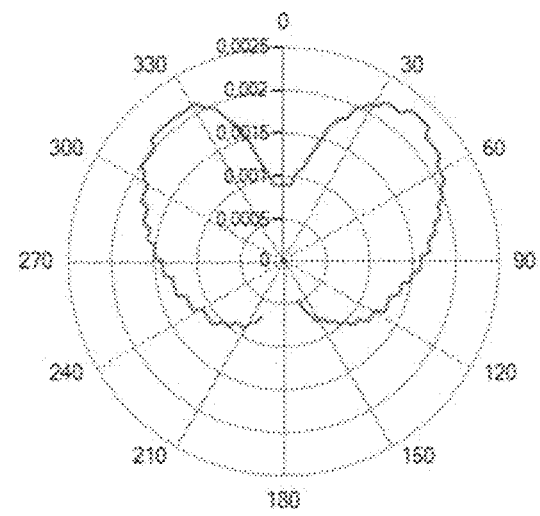

To obtain an improved distribution of the optical diffusion it is possible to adjust the various components that can form the diffuser 30. FIGS. 19, 20, 21 diagrammatically illustrate three embodiments of a light guide 27 comprising an optical fiber 28 and a diffuser 30. In the three embodiments illustrated the diffuser 30 comprises a core 30A and a sheath 30 that surrounds the core 30A. The two elements forming the diffuser 30 may both be diffusing, or one may be diffusing and the other transparent to the electromagnetic radiation propagated in the optical guide 27. In the embodiment of FIG. 19 both the core 30A, and the sheath 30B are made of diffusing material. In the embodiment of FIG. 20 the core 30A is made of the diffusing material and the sheath 30B is made of the transparent material. In the embodiment of FIG. 21 the core 30A is transparent and the sheath 30B is diffusing. FIGS. 22A-22I show the diagrams of electromagnetic radiation diffusion in various embodiments of the diffuser 30. FIGS. 22A-22D show the diffusion diagrams for a diffuser 30 made as shown in FIG. 20, that is to say with a diffusing core and a transparent outer sheath with a straight form. The four diagrams are obtained for different lengths of diffuser 30, namely 15 mm, 20 mm, 25 mm and 30 mm, respectively. By increasing the length of the diffuser 30 it can be seen that the loss of directive emission is more pronounced, whereas there is no particular effect on radial and back emission. To change the radial emission a different concentration or a different grain size of the diffusing powder contained in the core 30A is used. The diagram in FIG. 22E shows the emission of a diffuser 30 made with a diffusing core and a diffusing sheath and with a helical shape, with a single winding. The diagram in FIG. 22F illustrates the result obtained with the same diffuser, but with a straight shape.

Figure 22G:
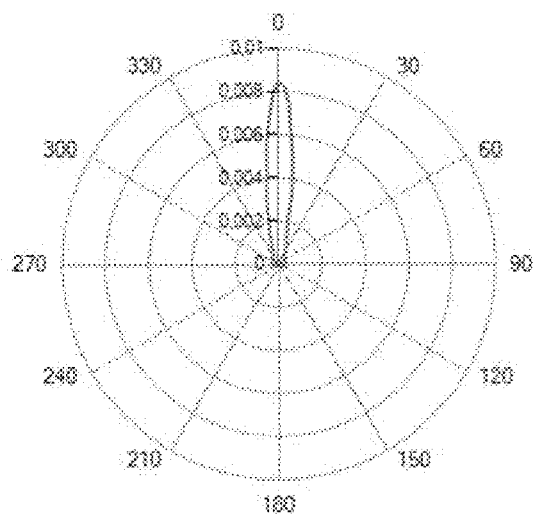
Figure 22H:
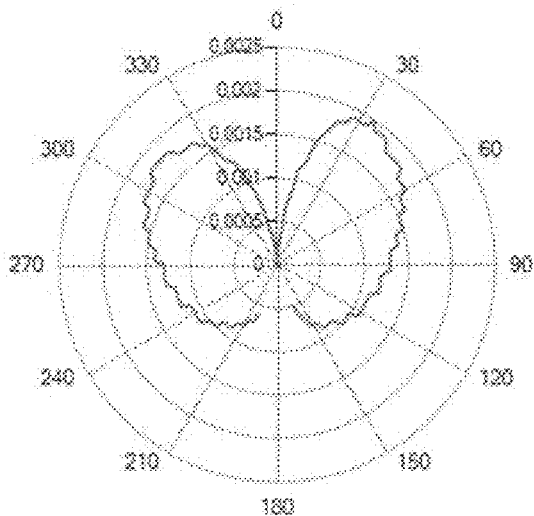
Figure 22I:
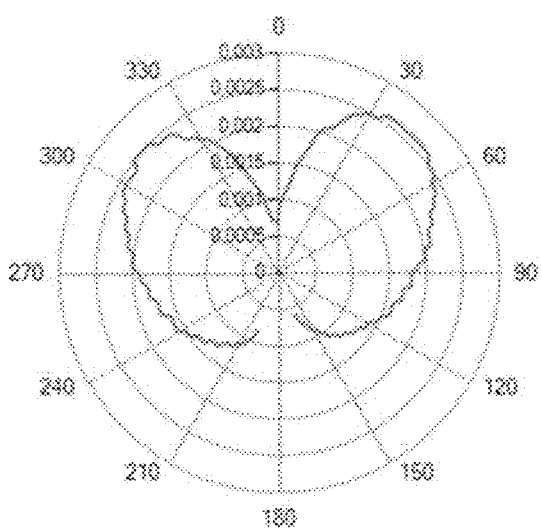

The diagrams of FIGS. 22G, 22H and 22I show the emission of a diffuser 30 having a transparent core and a diffusing sheath with the following geometric characteristics: as regards FIG. 22G the diffuser 20 is straight, in the case of FIG. 22H the diffuser has a helical development (FIG. 18) with two windings, and finally the diagram of FIG. 22I relates to the emission of a diffuser with a straight section and a helical section forming a single winding.

It can be noted that the radiation diagram of FIGS. 22G, 22H and 22I relating to a diffuser 30 with a helical portion are similar to the emission diagrams obtained with a diffusing sheath and a diffusing core (diagrams of FIGS. 22E, 22F), which however show difficulties in construction. The embodiment with transparent core and diffusing sheath with a diffuser having an at least partially helical shape (diagram of FIG. 22I) provides the most uniform lateral emission.

The diffuser 30 may have a tip of various shapes, as diagrammatically illustrated in FIGS. 23A, 23B and 23C. In FIG. 23A the diffuser 20 terminates with a truncated cone or truncated pyramid terminal element, in FIG. 23B a terminal element with a convex semi-spherical terminal element is provided, in FIG. 23C the terminal element has a concave semi-spherical shape. The shape of the tip of diffuser 30 may be selected according to the applications of the device 1, for example to achieve greater or lesser penetration of the radiation into the tissues treated.

The diffuser, both as regards the core and as regards the sheath, may be made of polymer material or quartz, for example. Radio-opaque powders may be introduced in the materials making up the diffuser, or a tip marker may be inserted for applications with X-ray monitoring.

The several features of the various embodiments disclosed above can be combined to one another in different ways, resulting in devices which may even be devoid of the first and second spacer.

The invention claimed is:

1. A device for laser thermal ablation, the device comprising:
    an outer tubular structure having a closed terminal end;
    an inner tubular structure positioned in the outer tubular structure, the inner tubular structure having a terminal end and the inner tubular structure defining an inner volume, the inner volume being configured to receive a light guide, wherein a coolant circulation gap is formed between the outer tubular structure and the inner tubular structure, wherein a spacer extends helically around a longitudinal axis of the outer tubular structure, the spacer being positioned between the outer tubular structure and the inner tubular structure, the spacer being in surface contact with an outer surface of the inner tubular structure and with an inner surface of the outer tubular structure, the spacer being configured to maintain the inner tubular structure and the outer tubular structure in a coaxial position, the spacer having turns distanced from one another to allow liquid circulation in the coolant circulation gap between the first tubular structure and second tubular structure.

2. The device as claimed in claim 1, wherein the light guide is housed in the volume of the inner tubular structure, wherein another gap for circulation of a coolant is formed between the inner tubular structure and the light guide.

3. The device as claimed in claim 2, wherein the light guide and the inner tubular structure are substantially coaxial at least in an end portion thereof, and another spacer is positioned between the light guide and a side wall of the inner tubular structure.

4. The device as claimed in claim 3, wherein the another spacer extends helically around an axis of the inner tubular structure and the spacer and the another spacer extend according to helical windings in opposite directions.

5. The device as claimed in claim 1, wherein the inner tubular structure comprises a side wall with at least one lateral opening, wherein the coolant circulation gap is in fluid communication with the inner volume of the inner tubular structure via the at least one lateral opening.

6. The device as claimed in claim 5, wherein a side wall of the inner tubular structure comprises a plurality of lateral openings, wherein the coolant circulation gap is in fluid communication with the inner volume of the inner tubular structure via the plurality of lateral openings.

7. The device as claimed in claim 6, wherein the lateral openings are arranged staggered from one another along a longitudinal extension of the inner tubular structure.

8. The device as claimed in claim 1, wherein the terminal end of the inner tubular structure is closed.

9. The device as claimed in claim 1, wherein the spacer is manufactured as component which is physically separate with respect to the inner tubular structure and to the outer tubular structure.

10. The device as claimed in claim 1, wherein the spacer is created separately from the inner tubular structure and the outer tubular structure.

11. A device for laser thermal ablation, the device comprising:
an outer tubular structure having a closed terminal end;
an inner tubular structure positioned in the outer tubular structure, the inner tubular structure having a side wall with a terminal end and the inner tubular structure defining an inner volume, wherein a first coolant circulation gap is formed between the outer tubular structure and the inner tubular structure;
a light guide housed in the inner volume of the inner tubular structure, wherein a second gap for circulation of a coolant is formed between the inner tubular structure and the light guide, wherein a spacer extends helically around a longitudinal axis of the inner tubular structure, the spacer being positioned between the inner tubular structure and the light guide, the spacer being in surface contact with an inner surface of the inner tubular structure and with the light guide, the spacer being configured to maintain the light guide in a coaxial position with the inner tubular structure, the spacer having turns distanced from one another to allow liquid circulation in the coolant circulation gap between the inner tubular structure and the light guide.

12. The device as claimed in claim 11, wherein the light guide comprises an optical fiber and a diffuser positioned between one end of the fiber and the terminal end of the inner tubular structure.

13. The device as claimed in claim 11, wherein the side wall comprises at least one lateral opening, wherein the coolant circulation gap is in fluid communication with the inner volume of the inner tubular structure via the at least one lateral opening.

14. The device as claimed in claim 13, wherein the side wall of the inner tubular structure comprises a plurality of lateral openings, the coolant circulation gap being in fluid communication with the inner volume of the inner tubular structure via the plurality of lateral openings.

15. The device as claimed in claim 14, wherein the lateral openings are arranged staggered from one another along a longitudinal extension of the inner tubular structure.

16. The device as claimed in claim 11, wherein the terminal end of the inner tubular structure is closed.

17. The device as claimed in claim 11, wherein the spacer is manufactured as component which is physically separate with respect to the inner tubular structure.

18. The device as claimed in claim 11, wherein the spacer is created separately from the inner tubular structure.

19. An apparatus for laser thermal ablation comprising:
a device comprising an outer tubular structure and an inner tubular structure, the outer tubular structure having a closed terminal end, the inner tubular structure being positioned in the outer tubular structure, the inner tubular structure having a terminal end and the inner tubular structure defining an inner volume, the inner volume being configured to receive a light guide, wherein a coolant circulation gap is formed between the outer tubular structure and the inner tubular structure, wherein a spacer extends helically around a longitudinal axis of the outer tubular structure, the spacer being positioned between the outer tubular structure and the inner tubular structure;
a laser source;
a cooling circuit;
a control unit.

20. The apparatus as claimed in claim 19, further comprising one or more of:
a pump for circulation of coolant;
a flow meter configured to detect a coolant flow rate;
a pressure sensor configured to detect a pressure of the coolant in at least one point of the cooling circuit;
a tank for feeding the coolant to the device;
a tank for collecting the coolant from the device;
a tank for storing and recirculating the coolant;
a member for removing heat from the coolant.

21. A device for laser thermal ablation, the device comprising:
an outer tubular structure having a closed terminal end;
an inner tubular structure positioned in the outer tubular structure, the inner tubular structure having a terminal end and the inner tubular structure defining an inner volume, wherein a first coolant circulation gap is formed between the outer tubular structure and the inner tubular structure;
a light guide arranged in the inner tubular structure, wherein a second coolant circulation gap is formed between the inner tubular structure and the light guide;
a first spacer extending helically around a longitudinal axis of the outer tubular structure, the first spacer being positioned in the first coolant circulation gap between the outer tubular structure and the inner tubular structure, wherein the first spacer is in surface contact with an inner surface of the outer tubular structure and with the outer surface of the inner tubular structure; and
a second spacer extending helically around a longitudinal axis of the inner tubular structure, the second spacer being positioned in the second coolant gap between the inner tubular structure and the light guide, wherein the second spacer is in surface contact with an inner surface of the inner tubular structure and with the light guide.

22. A device for laser thermal ablation, the device comprising:
an outer tubular structure having a closed terminal end;
an inner tubular structure positioned in the outer tubular structure, the inner tubular structure having a terminal end and the inner tubular structure defining an inner volume, wherein a first coolant circulation gap is formed between the outer tubular structure and the inner tubular structure;
a light guide arranged in the inner tubular structure, wherein a second coolant circulation gap is formed between the inner tubular structure and the light guide;
a first spacer positioned in the first coolant circulation gap between the outer tubular structure and the inner tubular structure adapted to maintain the first tubular structure and the second tubular structure approximately coaxial with one another, wherein the first spacer is in surface contact with an inner surface of the outer tubular structure and with the outer surface of the inner tubular structure; and
a second spacer extending helically around a longitudinal axis of the inner tubular structure, the second spacer being positioned in the second coolant gap between the inner tubular structure and the light guide, wherein the second spacer is in surface contact with an inner surface of the inner tubular structure and with the light guide.

* * * * *